(12) United States Patent
Rosinko et al.

(10) Patent No.: US 6,551,302 B1
(45) Date of Patent: *Apr. 22, 2003

(54) STEERABLE CATHETER WITH TIP ALIGNMENT AND SURFACE CONTACT DETECTOR

(76) Inventors: Michael J. Rosinko, 1614 Husted Ave., San Jose, CA (US) 95125; Alexander Khairkhahan, 1105 Lincoln Ave., Palo Alto, CA (US) 94301; Michael Horzewski, 6032 Running Springs Rd., San Jose, CA (US) 95136; Stuart D. Harman, 4321Beechmont Ave., San Jose, CA (US) 95136; Richard L. Mueller, 2305 Cypress Point, Byron, CA (US) 94514; Douglas R. Murphy-Chutorian, 151 Lowell Ave., Palo Alto, CA (US) 93401

( * ) Notice: Subject to any disclaimer, the term of this patent is extended or adjusted under 35 U.S.C. 154(b) by 43 days.

This patent is subject to a terminal disclaimer.

(21) Appl. No.: 09/697,672

(22) Filed: Oct. 26, 2000

Related U.S. Application Data

(63) Continuation-in-part of application No. 09/156,963, filed on Sep. 18, 1998, now abandoned.
(60) Provisional application No. 60/059,892, filed on Sep. 24, 1997.

(51) Int. Cl.[7] .............................................. A61M 31/00
(52) U.S. Cl. .......................... 604/505; 604/22; 604/28; 604/30; 604/31; 604/95.04; 606/13; 606/14
(58) Field of Search .............................. 604/22, 30, 31, 604/28, 505, 95.04; 606/13–15

(56) References Cited

U.S. PATENT DOCUMENTS 3,890,977 A   6/1975   Wilson ..................... 128/418
4,350,148 A   9/1982   Sivak, Jr. et al. ............ 128/4
4,586,923 A   5/1986   Gould et al. .................. 604/95

(List continued on next page.)

FOREIGN PATENT DOCUMENTS

| EP | 0 900 547 A1 | 3/1999 | |
| EP | 0 900 548 A1 | 3/1999 | |
| EP | 0 900 549 A1 | 3/1999 | |
| EP | 0 900 574 A1 | 3/1999 | |
| WO | WO 92/10142 | 6/1992 | ........... A61B/17/36 |
| WO | WO 97/47253 | 12/1997 | |
| WO | WO 98/05307 | 2/1998 | |
| WO | WO 98/39045 | 9/1998 | |

OTHER PUBLICATIONS

Deckelbaum, Lawrence I., M.D., "Cardiovascular Applications of Laser Technology," Lasers in Surgery and Medicine. No. 15, pp. 315–341, 1994.

Frazier, O.H., M.D. et al., "Mycardial Revascularization with Laser," Cullen Cardiovascular Research Laboratories, Texas Heart Institute; Dept. of Adult Cardiology, pp. II–58–II–65, 1995.

(List continued on next page.)

Primary Examiner—Linda C. M. Dvorak
Assistant Examiner—Henry M. Johnson, III
(74) Attorney, Agent, or Firm—Gibson, Dunn & Crutcher LLP

(57) ABSTRACT

A steerable percutaneous catheter for guiding at least one functional device to selected surfaces of a body for treatment thereon, particularly adapted for laser-assisted Percutaneous Transmyocardial Revascularization (PTMR). The steerable catheter has a handle portion at its proximal end and a controllably deflectable end portion at its distal end. The distal end of the catheter and the distal end of the functional device maintain alignment automatically during deflection. The invention also includes a surface contact detection system to detect contact with an interior body surface, such as the heart wall.

60 Claims, 14 Drawing Sheets

U.S. PATENT DOCUMENTS

| | | | |
|---|---|---|---|
| 4,658,817 A | 4/1987 | Hardy | 128/303.1 |
| 4,702,260 A | 10/1987 | Wang | 128/753 |
| 4,766,906 A | 8/1988 | Wang | 128/753 |
| 4,784,133 A | 11/1988 | Mackin | 128/303.1 |
| 4,846,171 A | 7/1989 | Kauphusman et al. | 128/303.1 |
| 4,911,148 A | 3/1990 | Sosnowski et al. | 128/6 |
| 4,920,980 A | 5/1990 | Jackowski | 128/786 |
| 4,960,134 A | 10/1990 | Webster, Jr. | 128/786 |
| 4,976,710 A | 12/1990 | Mackin | 606/15 |
| 5,006,997 A * | 4/1991 | Reich | 128/DIG. 12 |
| 5,030,204 A | 7/1991 | Badger et al. | 604/95 |
| 5,104,393 A | 4/1992 | Isner et al. | 606/15 |
| 5,114,402 A | 5/1992 | McCoy | 604/95 |
| 5,125,896 A | 6/1992 | Hojelbane | 604/95 |
| 5,190,050 A | 3/1993 | Nitzsche | 128/772 |
| 5,255,679 A | 10/1993 | Imran | 128/642 |
| 5,261,889 A | 11/1993 | Laine et al. | 604/164 |
| RE34,502 E | 1/1994 | Webster, Jr. | 607/125 |
| 5,279,596 A | 1/1994 | Castaneda et al. | 604/282 |
| 5,307,803 A | 5/1994 | Matsuura | 128/4 |
| 5,358,479 A | 10/1994 | Wilson | 604/95 |
| 5,380,316 A | 1/1995 | Aita et al. | 606/7 |
| 5,386,837 A | 2/1995 | Sterzer | 128/898 |
| 5,389,096 A | 2/1995 | Aita et al. | 606/15 |
| 5,397,304 A | 3/1995 | Truckai | 604/95 |
| 5,409,453 A * | 4/1995 | Lundquist et al. | 604/22 |
| 5,423,743 A * | 6/1995 | Butterfield | 128/DIG. 13 |
| 5,431,168 A | 7/1995 | Webster, Jr. | 128/658 |
| 5,464,394 A | 11/1995 | Miller et al. | 604/96 |
| 5,465,717 A | 11/1995 | Imran et al. | 128/642 |
| 5,489,270 A | 2/1996 | van Erp | 604/95 |
| 5,498,238 A | 3/1996 | Shapland et al. | 604/53 |
| 5,514,128 A | 5/1996 | Hillsman et al. | 606/7 |
| 5,533,957 A * | 7/1996 | Aldea | 128/898 |
| 5,554,114 A | 9/1996 | Wallace et al. | 604/53 |
| 5,571,151 A | 11/1996 | Gregory | 607/88 |
| 5,607,421 A | 3/1997 | Jeevanandam et al. | 606/15 |
| 5,685,853 A | 11/1997 | Bonnet | 604/164 |
| 5,827,278 A | 10/1998 | Webster, Jr. | 606/41 |
| 5,840,059 A | 11/1998 | March et al. | 604/53 |
| 5,843,076 A | 12/1998 | Webster, Jr. et al. | 606/41 D |
| 5,848,986 A * | 12/1998 | Lundquist et al. | 604/22 |
| 5,860,951 A * | 1/1999 | Eggers et al. | 604/22 |
| 5,876,373 A | 3/1999 | Giba et al. | 604/95 |
| 5,897,529 A | 4/1999 | Ponzi | 604/95 |
| 5,904,666 A * | 5/1999 | DeDecker et al. | 604/131 |
| 5,925,012 A | 7/1999 | Murphy-Chutorian et al. | 604/30 |
| 5,941,872 A * | 8/1999 | Berg | 604/500 |
| 5,964,757 A | 10/1999 | Ponzi | 606/45 |
| 5,999,678 A * | 12/1999 | Murphy-Chutorian et al. | |
| 6,013,072 A * | 1/2000 | Winston et al. | |
| 6,024,703 A | 2/2000 | Zanelli et al. | 600/437 |
| 6,024,739 A * | 2/2000 | Ponzi et al. | 600/374 |
| 6,102,886 A * | 8/2000 | Lundquist et al. | 604/22 |
| 6,165,188 A * | 12/2000 | Saadat et al. | 604/22 |
| 6,179,809 B1 | 1/2001 | Khairkhahan et al. | 604/95.04 |
| 6,183,444 B1 | 2/2001 | Glines et al. | 604/187 |

OTHER PUBLICATIONS

Duerig, T.W., and A.R. Pelton, "Structure and Properties of Ti–Ni Alloys," In Press, Titanium Handbook, ASM, 1994.

http://www.annurev.org/sup/im/im15/im15b.htm.

http://www.darwin.bio.uci.edu/~cchughes/index.html.

http://www.annurev.org.

Deckelbaum, Lawrence I, M.D., "Cardiovascular Applications of Laser Technology," Lasers in Surgery and Medicine 15:315–341, 1994.

Frazier, O.H., M.D. et al.. "Mycardial Revascularization with Laser," Cullen Cardiovascular Research Laboratories, Texas Herat Institute, II–58–II–65, 1995.

* cited by examiner

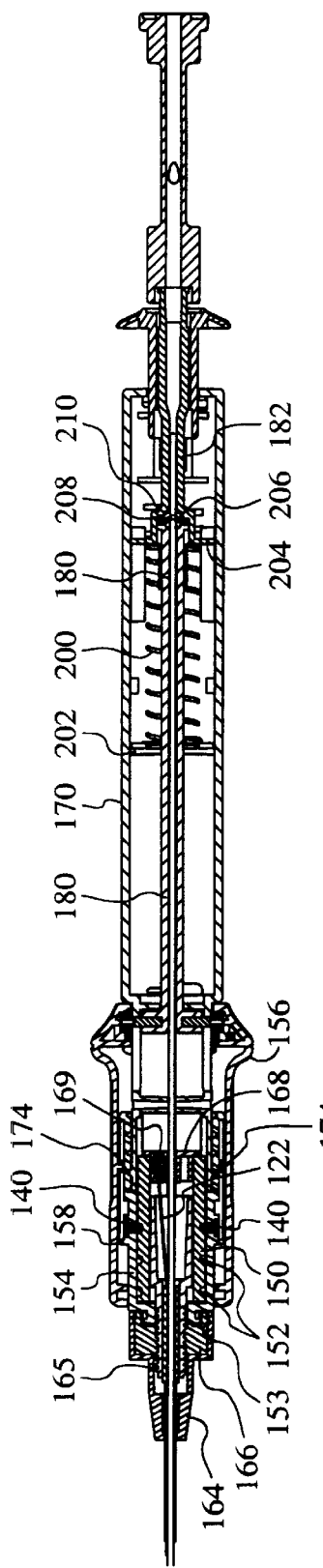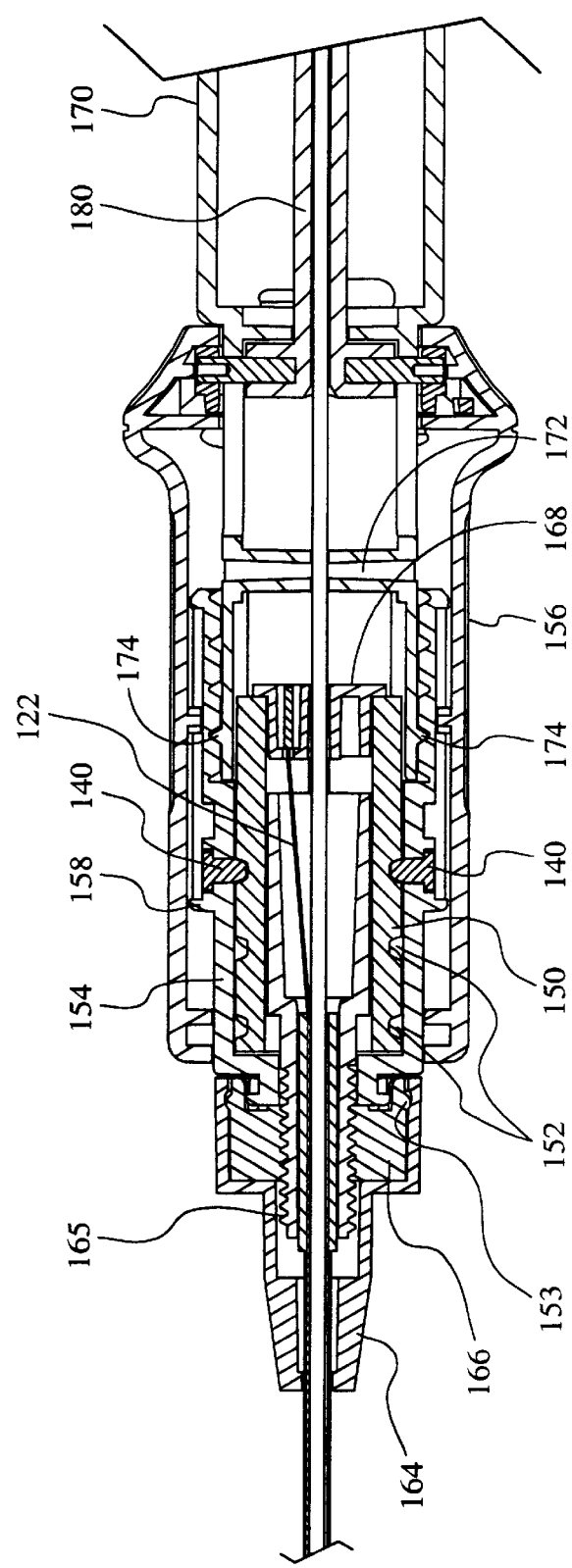
FIG. 5A
FIG. 5AA

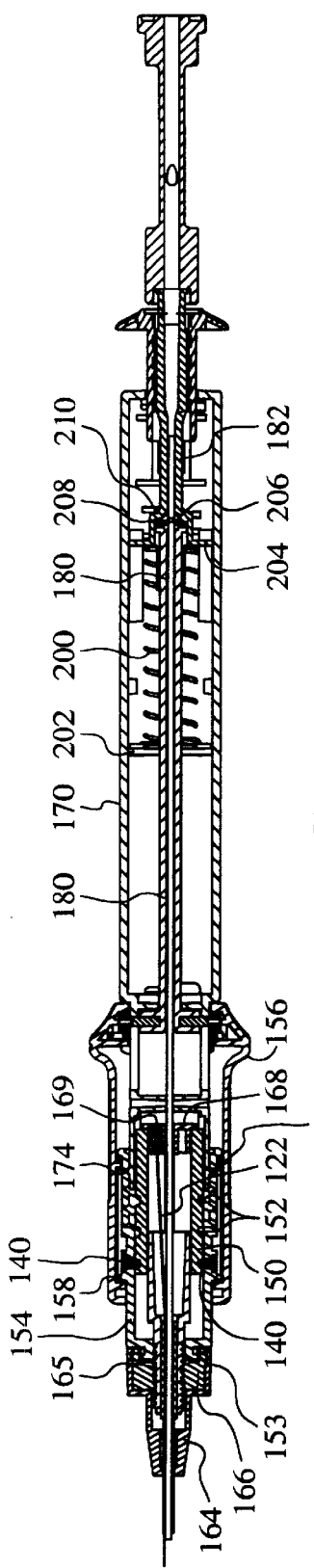
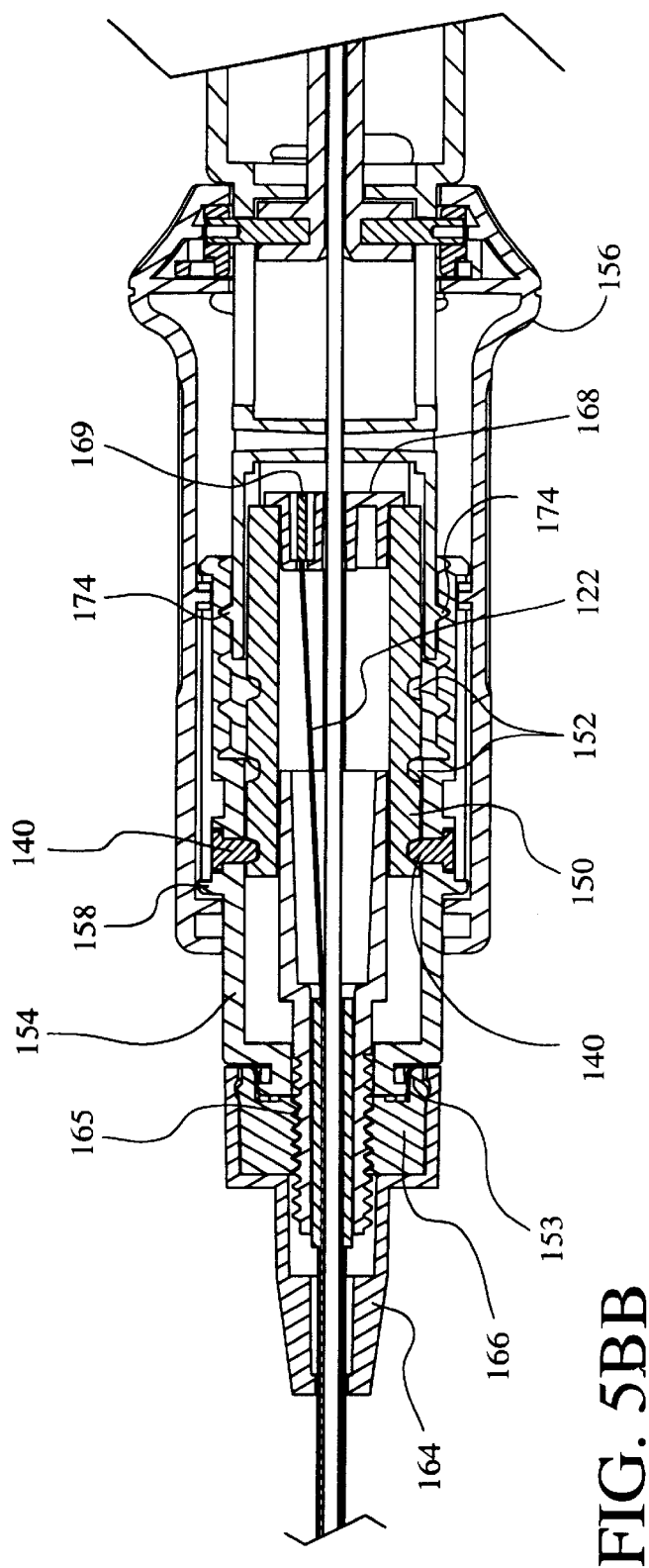
FIG. 5B
FIG. 5BB

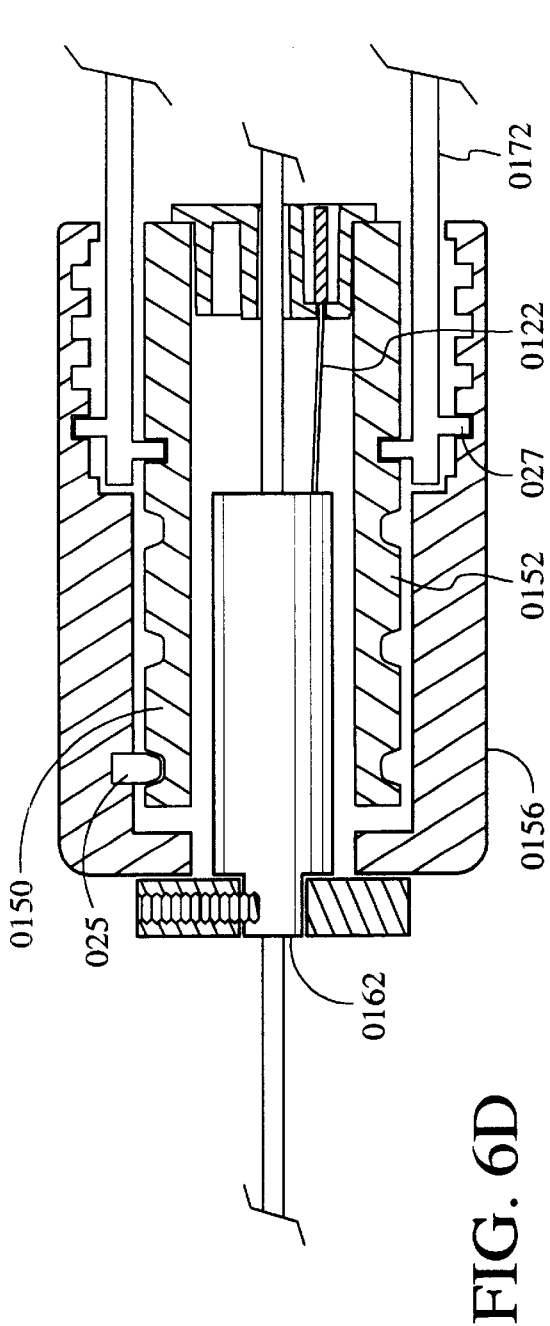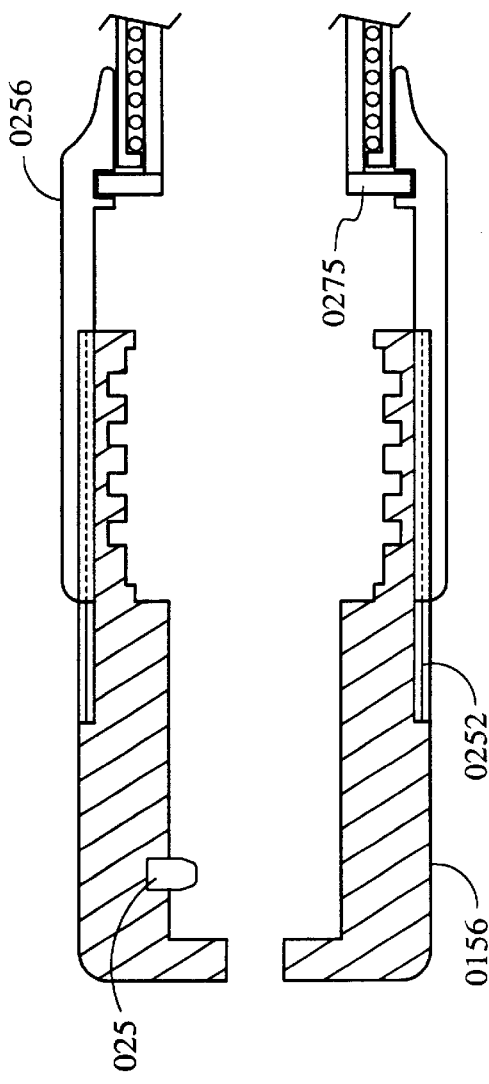
FIG. 6D
FIG. 6E

STEERABLE CATHETER WITH TIP ALIGNMENT AND SURFACE CONTACT DETECTOR

PRIORITY CLAIM

This Application is a continuation-in-part of U.S. application Ser. No. 09/156,963 filed Sep. 18, 1998 now abandoned entitled STEERABLE CATHETER WITH TIP ALIGNMENT AND SURFACE CONTACT DETECTOR which claims the benefit of domestic priority under 35 U.S.C. section 119(e) from U.S. Provisional Application Ser. No. 60/059,892 filed Sep. 24, 1997 entitled FIBER/CATHETER TIP ALIGNMENT, both of which are herein incorporated by reference in their entirety.

CROSS-REFERENCE TO RELATED APPLICATIONS

The following application is hereby incorporated by reference: application Ser. No. 09/156,964, now U.S. Pat. No. 6,179,809, entitled "DRUG DELIVERY CATHETER WITH TIP ALIGNMENT."

FIELD OF INVENTION

The present invention relates generally to steerable catheters and catheter procedures involving functional devices, such as laser delivery devices and drug delivery devices. More particularly, the invention relates to a steerable catheter and method of use, particularly adapted for laser-assisted Percutaneous Transmyocardial Revascularization (PTMR). The distal tip of the catheter for guiding a laser delivery device, drug delivery device or other functional device extendable there through, is deflectable in at least one given plane. The invention includes an automatic catheter tip alignment system for maintaining constant relative positioning between the distal tip of the functional device and the distal tip of the steerable catheter. The invention also includes a surface contact detection system to detect contact with an interior body surface, such as the heart wall.

BACKGROUND OF INVENTION

In the treatment of heart disease, one method of improving myocardial blood supply is called transmyocardial revascularization (TMR), the creation of channels in the myocardium of the heart. The procedure using needles in a form of surgical "myocardial acupuncture" has been used clinically since the 1960s. Deckelbaum. L. I., Cardiovascular Applications of Laser Technology, *Lasers in Surgery and Medicine* 15:315–341 (1994). The technique relieves ischemia by allowing blood to pass from the ventricle through the channels either directly into other vessels communicating with the channels or into myocardial sinusoids which connect to the myocardial microcirculation.

In the reptilian heart, perfusion occurs via communicating channels between the left ventricle and the coronary arteries. Frazier, O. H., Myocardial Revascularization with Laser-Preliminary Findings, *Circulation,* 1995; 92 [suppl II]:II-58-II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures has recurred with the advent of medical lasers used to create TMR channels. Histological evidence of patent, endothelium-lined tracts within laser-created channels shows that the lumen of laser channels can become hemocompatible and resists occlusion. A thin zone of charring occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the surface of the heart to create the desired number of channels.

The foregoing discussion relates to surgical procedures, i.e. procedures which access the heart surgically, either via open heart surgery, or perhaps by minimally invasive surgical (MIS) methods if the design and size of the distal ends of the hand pieces are suitable for use in an MIS site. However, since TMR most often involves creating channels through the epicardium into the lower left chamber of the heart, it is desirable to create TMR channels in a percutaneous procedure, i.e. by extending a catheter apparatus through the vasculature into the ventricle and creating the channels through endocardial surfaces and into myocardium. Performing percutaneous TMR (PTMR) is desirable for a number of reasons. Percutaneous catheter procedures are typically less traumatic to the patient compared to surgical procedures. Adhesions between the pericardial sac and epicardium are eliminated. Percutaneous TMR with a catheter apparatus also offers an alternative solution to persons who are not candidates for surgical procedures.

Because TMR procedures generally involve creating a plurality of channels within the myocardium, performing the procedure percutaneously requires the ability to steer a catheter apparatus through the vasculature and maneuver the apparatus within the ventricle of the beating heart as rapidly as possible to create the channels without subjecting the heart to the undue stress of a lengthy procedure. Additionally, the ability to control and stabilize the catheter apparatus against the beating heart wall while creating channels with a laser is desirable for percutaneous procedures to ensure creation of channels as desired and to ensure that the laser, or other energy source, is fired only within the myocardial tissue. For example, if the energy source is activated prior to wall contact, such activation may lead to the coagulation of blood and result in emboli. TMR channels should be spaced and grouped appropriately to achieve the desired result without weakening or rupturing the heart muscle.

The early myocardial acupuncture procedures were not performed percutaneously. The Hardy $CO_2$ laser delivery system described above is rigid, relatively large, and not adaptable for percutaneous use. The Aita '316 patent does not suggest a method for percutaneous use of the laser delivery device described therein for surgical use.

U.S. Pat. No. 5, 389,096 issued Feb. 14, 1995 to Aita et al. purports to teach one method of percutaneous TMR using an elongated flexible lasing apparatus with control lines and a focusing lens structure at the distal tip. The method uses pressure applied manually to attempt to stabilize the apparatus against the wall of the heart.

Several patents describe the use of catheters within the ventricle for percutaneous treatment of ventricular tachycardia. Such devices have a means to locate an arrhythmia site and ablate the site, at or just below the ventricle surface, using an electrode device or laser energy. U.S. Pat. No. 5,104,393 issued Apr. 14, 1992 to Isner teaches a catheter apparatus having a guiding Y-shaped sheath and guide catheter assembly for introducing an optical fiber into the ventricle. Positioning is described to enable a single burst of laser energy from a single aperture to ablate the site.

U.S. Pat. No. 5,255,679 issued Oct. 26, 1993 and U.S. Pat. No. 5,465,717 issued Nov. 14, 1995 respectively to Imran and Imran et al., disclose non-laser, basket-shaped catheter apparatus for mapping and/or ablation of arrhythmia sites within the ventricle. A pull cable is used to expand the basket portion within the ventricle, and a plurality of electrodes on the arms of the basket are used for ablation. The basket device is designed to place the electrodes on the ventricle wall.

U.S. Pat. No. 5,190,050 issued Mar. 2, 1993 to Nitzsche teaches a steerable catheter with a handle and a tube, the distal tip of which may be selectively curved by controllably moving one of three flat, sandwiched shims relative to the others by manipulation of a handle portion.

U.S. Pat. No. 5,358,479 issued Oct. 25, 1994 to Wilson, incorporated herein in its entirety by reference, teaches another steerable catheter with a handle and an inner tube, the apparatus having a single elongated, substantially flat shim spring mounted within the tip of the catheter tube, the shim having at least one transverse or lateral twist which causes the tip of the catheter tube to assume a desired curvature.

Drug therapies with angiogenic growth factors may expedite and/or augment collateral artery development. U.S. Pat. No. 5,498,238 issued Mar. 12, 1996 to Shapland et al., discloses a method simultaneous angioplasty and drug delivery to localized portions of arteries. The patent teaches the use of an expandable balloon end type catheter which can be filled with a drug-containing fluid and which is allowed to permeate through a semi-permeable membrane of the balloon-tip end and thereby be delivered directly to the surface of arteriosclerotic lesions on stenosed arteries.

A great deal of published scientific information concerning therapeutic agents is currently available on the internet. One company, Annual Reviews is located at http://www.annurev.org. A list of genetically engineered and/or naturally occurring drugs or other agents having pharmacological, therapeutic, diagnostic or other utility is located at http://www.annurev.org/sup/in/im15/im15b.htm. Additional scientific information is available at http://darwin.bio.uci.edu/cchughes/index.html.

Devices for effectuating drug injection have included non-articulating, viewing devices. U.S. Pat. No. 5,685,853 issued Nov. 11, 1997 to Bonnet teaches of a partially rigid endoscope to which is attached an injection or aspiration cannula that is axially adjustable along the shaft of the endoscope.

U.S. Pat. No. 5,261,889 issued Nov. 16, 1993 to Laine et al. teaches of an injection therapy catheter that is insertable through a working channel in an endoscope for delivering fluid agents through a hollow needle at the distal end of the catheter.

U.S. Pat. No. 5,685,853 issued Nov. 11, 1997 to Bonnet teaches an injection device by means of an injection cannula axially adjustable along an endoscope shaft. The injection cannula and guide tube are axially adjustable relative to the endoscope shaft by means of a handle which can be operated with one hand.

U.S. Pat. No. 4,350,148 issued Sep. 21, 1982 to Sivak, Jr. et al. also teaches of a drug injector device, in this case for treating esophageal varices. A flexible shafted endoscope has a conduit with distal ended needle is inserted in the endoscope's biopsy channel for effectuating the treatment.

Prior devices also include viewing devices for cardiac interventional procedures. U.S. Pat. No. 4,784,133 issued Nov. 15, 1988 and U.S. Pat. No. 4,976,710 issued Dec. 11, 1990, both to Mackin, both teach of a flexible angioscope/bronchoscope device with an inflatable balloon structure for viewing intravasculature structures. These flexible catheter devices include a ported working channel for introduction of a working device and positioning of the working device at the viewing/treatment distal end.

U.S. Pat. No. 5,554,114 issued Sep. 10, 1996 to Wallace et al. teaches an infusion device with preformed shape. An infusion guidewire or catheter is used for introduction of the device through a selected path in a patient's vascular system. An elongated tubular diffusion body lies at the distal end of an elongated tube, the diffusion portion having a plurality of infusion ports through which blood, drug, diagnostic agent or other material can be delivered to the particular site in the vascular system.

U.S. Pat. No. 5,464,394 issued Nov. 7, 1995 to Miller et al. teaches a multilumen percutaneous angioscopy catheter which allows simultaneous irrigation and passage of an angioscope there through.

U.S. Pat. No. 4,702,260 issued Oct. 27, 1987 and U.S. Pat. No. 4,766,906 issued Aug. 30, 1988, both to Wang, teach bronchoscopic needle assemblies. The needle assemblies are especially adapted for safe and efficacious collection of biopsy samples.

U.S. Pat. No. 5,409,453 issued Apr. 25, 1995 to Lundquist et al. teaches a steerable medical probe with stylets. The device is designed for reducing the mass of a body part, such as for biopsy sampling or for removing prostatic tissue in the case of BPH. The torquable catheter has a control end and a probe end, the probe end having a stylet guide means with a flexible tip and a tip directing means extending from the control end to the flexible tip for changing the orientation of the central axis of the stylet guide means for directing a flexible stylet outward through the stylet port and through intervening tissue to targeted tissues.

U.S. Pat. No. 5,571,151 issued Nov. 5, 1996 to Gregory teaches a method for contemporaneous application of laser energy and localized pharmacologic therapy. The method comprises preparing a solution of a pharmacologic agent, inserting the catheter into the lumen, directing the catheter to the site, transmitting visible light to the site, flowing the light transmissive liquid through the catheter, viewing the site, transmitting laser energy through the liquid filled catheter to treat the site, and introducing a flow of the pharmacologic agent in solution into the catheter for contemporaneous discharge at the distal end into the lumen adjacent the site.

International Publication No. WO 92/10142 published Jun. 25, 1992 by Pfizer Hospital Products Group and Makower teaches a device and method for interstitial laser energy delivery. A catheter with moveable needle system places one or more fiber optic elements and thermo-measuring devices through a body passageway wall and into the bulk of an adjacent organ. The catheter is positioned adjacent to the organ and the needles are extended to mechanically puncture the wall and move into the organ with the fiber optic elements. The needle may be withdrawn into the catheter before delivery of laser energy or remain in the organ to serve as an aspiration-irrigation vehicle. Lumens provided within the catheter for carrying the hollow needles may likewise be used for respiration or irrigation of the passageway. The devices may also be used with a dilatation balloon, etc.

U.S. Pat. No. 5,386,837 to Sterzer discloses an "electro-chemotherapeutic" technique for treating tumors in which high intensity electromagnetic force fields (including a laser) are applied to the body after chemotherapy has been applied. This is intended to create large, transient pores in individual cells of a superficially-seated tumor lesion located between individually mounted ceramic horn antennae by non-invasively applying a highly directional beam of force-field shock of HF pulsed wave energy into the cells, thus inducing the drug to enter the cells.

The use of superelastic and/or shape memory materials is widely known. *Structure and Properties of Ti—NI Alloys: Nitinol Devices & Components*, Duerig et al., In Press, Titanium Handbook, ASM (1994) In general, binary compositions of Nickel (Ni) and Titanium (Ti), yield alloys with shape memory and superelastic properties. These alloys are commonly referred to as Ni—Ti, nitinol, and other industry names. Their precise physical and other properties of interest are extremely sensitive to the precise Ni/Ti ratio used. Generally, alloys with 49.0 to 50.7 atomic % of Ti are commercially available, with superelastic alloys in the range of 49.0 to 49.4%, and shape memory alloys in the range of 49.7 to 50.7%. Due to a rapid decrease in the ductility of the material, binary alloys with less than 49.4 at. % Ti are generally unstable. In general, these types of materials exhibit hysteresis, defined as a phenomenon exhibited by a system whose state depends on its previous history, and illustrated diagrammatically by the familiar upper and lower curves which meet at the ends and define an area under the curves. In the case of solid materials undergoing elastic hysteresis (as opposed to magnetic or electrical hysteresis), the curves are related to stress necessary to cause deformation or otherwise overcome existing stress in pre-stressed materials.

For the purposes of this disclosure, a distinction between superelastic materials and shape memory materials is made. Superelasticity refers to the highly exaggerated elasticity, or springback, observed in many Ni—Ti alloys deformed at a specific temperature. The function of the material in many of such cases is to store mechanical energy. Though limited to a rather small temperature range, these alloys can deliver over 15 times the elastic motion of a spring steel, i.e., withstand a force up to 15 times greater without permanent deformation. Shape memory materials will refer to those materials which can be deformed, but which will freely recover their original shapes during heating, often utilizing electrical resistivity, or which will develop a large recovery stress when recovery is prevented. With regard to the present invention, it will be understood that the transition temperature of materials must, in general, be somewhat above body temperature.

U.S. Pat. No. 3,890,977 issued Jun. 24, 1975 to Wilson teaches kinetic memory electrodes, catheters and cannulae. These devices incorporate a material, such as a Ni—Ti alloy, having heat-activated mechanical memory properties. The device is formed into an operative shape at a high temperature. Then, at a low temperature below its transitional temperature, it is reformed into a shape for ease of insertion into a guide catheter or the like or otherwise through a portion of a patient's vasculature or other body lumen. When located in the organ or other desired region, those portions of the device constructed using such shape memory materials are heated to above their transitional temperatures, using electrically resistive elements, thereby returning the catheter to its original annealed anchoring or proper locating shape. An important drawback of the Wilson apparatus is that heat must be applied to the catheter tip. Complicated construction and electrical power distribution must be considered.

U.S. Pat. No. 5,114,402 issued May 19, 1992 to McCoy teaches a maneuverable distal apparatus with a temperature activated material of construction which, upon heating to a predetermined position, will assume a predetermined, memorized shape, and which upon cooling, will assume a different shape by action of a spring element urging the apparatus into the different shape.

U.S. Pat. 4,846,171 issued Jul. 11, 1989 to Kauphusman et al. teaches a transluminal angioplasty catheter with a fiber advancing housing with a Hall effect sensor for control of a laser irradiation source that cooperates with the fiber advance mechanism.

There is a need for steerable percutaneous catheters, especially PTMR steerable catheters which automatically maintain alignment of the distal end of the catheter with the distal end of a functional device therein during catheter deflection movement relative to an interior body surface, particularly a ventricular wall. Moreover, there is a need for a mechanism to detect interior body surface contact with the distal tip of the catheter.

ADVANTAGES AND SUMMARY OF INVENTION

Thus, it is an advantage of the present invention to provide a steerable catheter and method of use for percutaneous and other intra-vascular procedures, including but not limited to PTMR, or any stimulation procedure.

The steerable percutaneous catheter of the present invention comprises a catheter jacket having proximal and distal ends, and at least a first lumen, at least a first one functional device within the lumen of the catheter jacket, the functional device having proximal and distal ends, a deflection mechanism at the proximal end of the catheter, the deflection mechanism operatively attached to a deflector device at the distal end of the catheter jacket, activation of the deflector device by movement of the deflection mechanism deflects the distal end of the catheter jacket and the functional device therein; and a relative movement compensation mechanism for maintaining. alignment between the catheter jacket and the functional device whereby movement of the deflecting mechanism causes simultaneous movement of the relative compensation movement mechanism.

It is a further advantage of the present invention to provide a steerable catheter capable of being guided into a heart chamber and used therein for creating a plurality of TMR channels controllably and efficiently that can maintain tip alignment during motions of the distal section of the catheter. It is a further advantage of the present invention to provide an elongated steerable catheter for placement within a heart chamber, organ aperture or other body opening, the steerable catheter having an inner tube extending there through, the inner tube for guiding a laser delivery device or other functional device to selected surfaces of the heart chamber, organ aperture or other body opening or body surface for laser or other treatment thereon, particularly adapted for laser-assisted transluminal revascularization (TMR) and further including a mechanism for maintaining a constant positional relationship between the translatable laser delivery device or other functional device and the distal tip of the catheter during catheter tip deflection.

It is yet a further advantage of the present invention to provide a percutaneous steerable catheter which can be positioned securely into a selected position within the left ventricle, or other body opening or cavity.

A further advantage of the present invention is to provide a steerable catheter with a tip alignment system which maintains precise alignment between the distal tip of the catheter and a laser delivery device such as fiber, bundle, other functional devices being inserted there through, etc., as the distal tip of the steerable catheter is deflected.

A further advantage of the present invention is to provide a steerable catheter which can be used for detection of contact and maintenance of contact between the distal tip of the catheter and the heart wall or other interior body structure or surface, such as during PTMR or stimulation.

A further advantage is to provide a steerable catheter with a handle portion at its proximal end and a controllably deflectable portion at its distal end.

The elongated corner or inner tube has a distal end, in the region where a curvature is to be formed, and an anchor sleeve is slidably disposed over the center or inner tube. The anchor sleeve is attached to the inside wall of the outer jacket and coupled to the distal end of the center or inner tube with a bendable member which extends between the distal tip of the steerable catheter and the anchor sleeve over the center or inner tube in a first embodiment. In a second embodiment of the center or inner tube, a shim is attached to the sleeve and a coil on the proximal end and is positioned in a key hole configuration. The distal section of the shim is attached to the distal tip of the catheter.

On the opposite the translation sleeve is a guide for a pull cable, the pull cable attached to the distal end of the steerable catheter and extending through the guide to the handle. Thus, the translation sleeve is maintained radially opposite the pull cable with the center or inner tube in between. An alternate design includes a spring in which a pull wire is attached to the distal end of the catheter without the shim.

An outer jacket has, in a preferred embodiment, distinct sections of different stiffness or durometer. One or more distinct sections of material of differing stiffness or durometer can be used. Junctions between the sections of different stiffness or durometer can be discrete and clearly defined, or they can blend smoothly or gradually. A distal, more flexible portion is coupled to a proximal, stiffer portion. The anchor sleeve is coupled to the outer jacket at or near the junction of two portions of the outer jacket in a first embodiment of the catheter body. A second embodiment has the shim coupled to the sleeve. Thus, the center tube moves freely through the anchor sleeve Adjacent the handle, the proximal outer jacket portion terminates at the catheter base. The pull cable extends through the catheter base, through a deflection housing tube, and terminates in a cable stop. Rotation of a deflection knob threadably mounted onto the deflection housing tube will cause the pull cable to be pulled backward, or the outer jacket to be pushed forward, relative to each other, thereby inducing deflection of the distal end of the steerable catheter. Additionally, another degree of deflection can be implemented by use of an additional deflection wire at the distal catheter tip that is controlled by a knob or slide member on the catheter handle to achieve at least two degrees of deflection freedom at the catheter tip.

The elongated steerable catheter is designed to be placed into the vasculature of the patient and steered there-through until the distal tip is adjacent a selected portion of tissue, such as on an endocardial surface within the left ventricle. Thus, the distal tip of a laser delivery device, such as an optical fiber or fiber bundle or other functional energy delivery device such as radio frequency electrodes, microwave cutters, ultrasound transmitters, mechanical coring devices, fluids jets and the like, can be extended through the inner tube of the steerable catheter such that its distal tip comes into contact with the selected surface structure for treatment thereon. With regard to PTMR therefore, the energy delivery device can be controllably advanced through the steerable catheter for creating one or more PTMR channels. Furthermore, with regard to non-laser PTMR, a cannula or trocar assembly may be extended through the steerable catheter into the tissue of the ventricle, with or without use of a mechanical piercing tool.

In alternate embodiments, the steerable catheter of the present invention includes other functional devices including but not limited to, fiber advance depth control mechanism, visualization device, drug delivery apparatus, etc.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 5A is a representative sectional view of a preferred embodiment of the handle of the steerable catheter of the present invention using a rotatable differential screw mechanism with an integrated functional device advance mechanism for achieving auto-alignment of the distal tip of the catheter and functional device in an un-deflected position.

FIG. 5AA is an enlarged view of detail 5A.

FIG. 5B is a representative section view of a preferred embodiment of the handle of the steerable catheter of the present invention using a rotatable differential screw mechanism with an integrated functional device advance mechanism for achieving auto-alignment of the distal tip of the catheter and functional device in a deflected position.

FIG. 5BB is an enlarged view of detail 5B.

FIG. 6D is a partial cut-away view of a second embodiment of the handle using a rotatable differential screw mechanism showing fiber advance and deflection components for achieving auto-alignment of the fiber optical tip.

FIG. 6E is a cross-sectional view of a variation of the embodiment shown in FIGS. 5C–E and 6A of the handle device using an integrated rotatable differential screw with an integrated fiber advance mechanism for achieving auto-alignment of the optical fiber tip.

DETAILED DESCRIPTION

Figure 1:
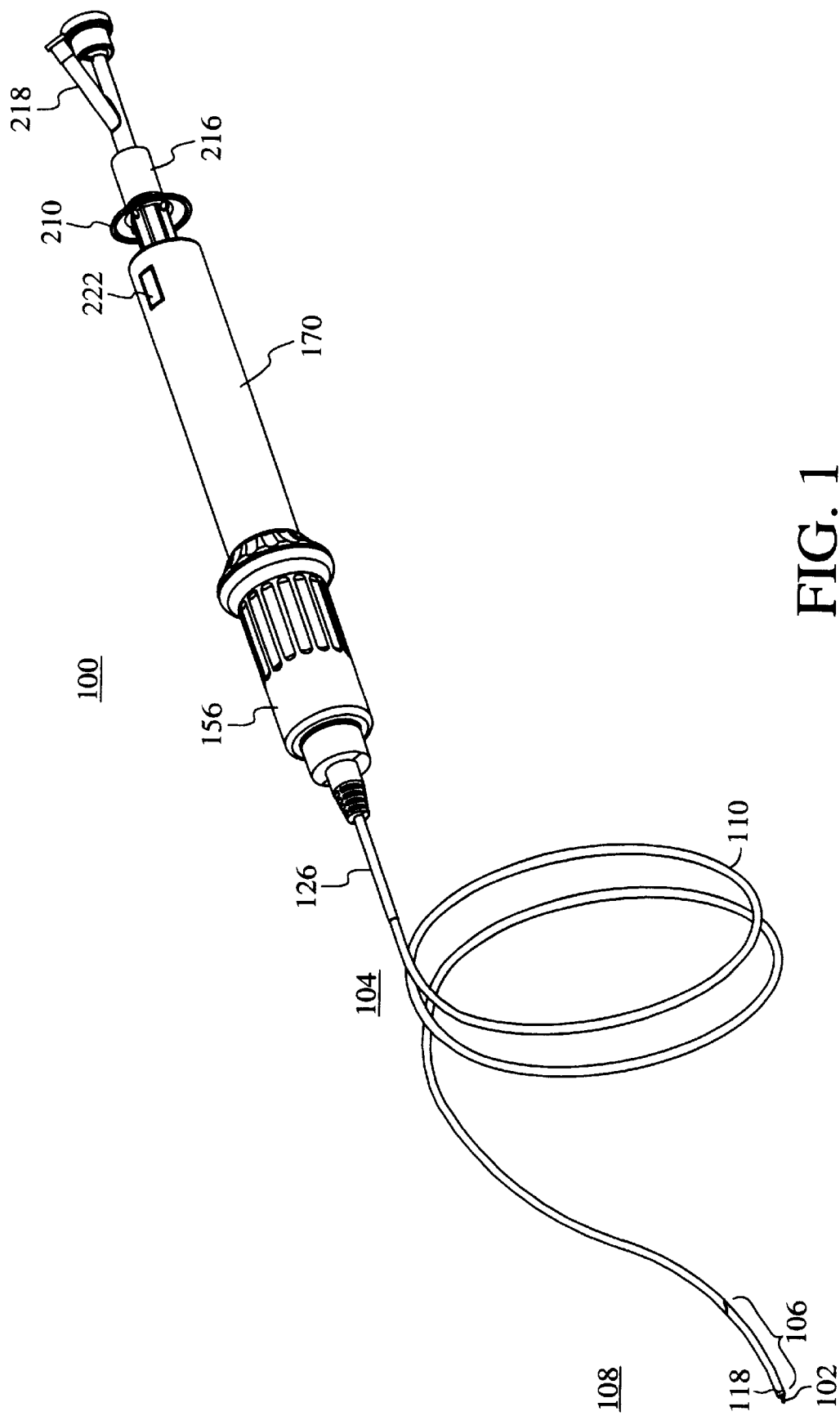
FIG. 1 is a representative isometric view of a preferred embodiment of the steerable catheter of the present invention showing a handle having an actuator and deflective end portion.

FIG. 1 is a representative isometric view of a preferred embodiment of the steerable catheter 100 of the present invention showing a handle having an actuator 156 and deflective end portion 106 with the distal tip of a functional device 102. A preferred embodiment of the catheter 100 has a handle 170 at its proximal end 104 and a controllably deflectable end portion 106 at its distal end 108. The deflectable end portion 106 is more flexible than the elongated catheter jacket 110, allowing the deflectable end portion 106 to develop a controlled bend with a small radius of curvature.

Components for effectuating multiple degrees of freedom of the distal tip of the catheter as well as other features for steerable catheter systems are disclosed in U.S. patent application Ser. No. 08/833,352 entitled STEERABLE CATHETER by Giba et al. filed Apr. 4, 1997, which is hereby incorporated by reference in its entirety.

Figure 2A:
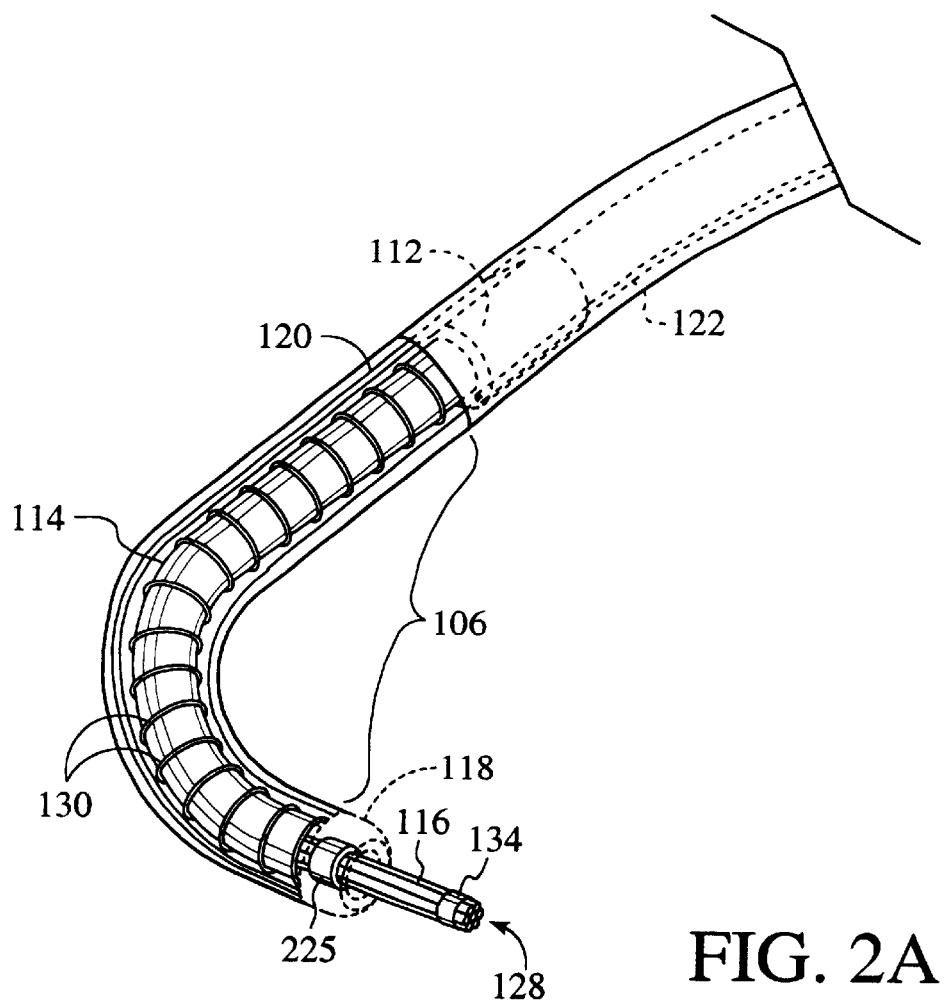
FIG. 2A is a representative partial cutaway view of the deflectable end portion and anchor sleeve of a preferred embodiment of the steerable catheter system of the present invention.

FIG. 2A is a representative partial cutaway view of the deflectable end portion 106 and anchor sleeve 112 of a preferred embodiment of the steerable catheter 100 of the present invention. As will be understood by the drawings and description herein, the curvature in the deflectable end portion 106 of the inner tube 114 can be deflected as desired. The helical coil spring 130 can be constructed with varying degrees of flexibility, and with any number of coils, such that the curvature can be moved closer to the catheter tip 118 of the inner tube 114 or closer to the anchor sleeve 112. As will be understood, increasing the tension in pull cable 122, attached at a location near the catheter tip 118, by retraction thereof will cause deflection of the catheter tip 118 and the deflectable end portion 106 in a direction essentially out of, and into and toward a position perpendicular to the plane of the shim 120. Continued retraction of the pull cable 122 will cause continued deflection of the catheter tip 118 and deflection of end portion 106 of the steerable catheter, with useful ranges of deflection between about 0 and about 180 degrees (U shape) to about 270 degrees (pig-tail shape), or more or less depending upon construction.

Figure 2B:
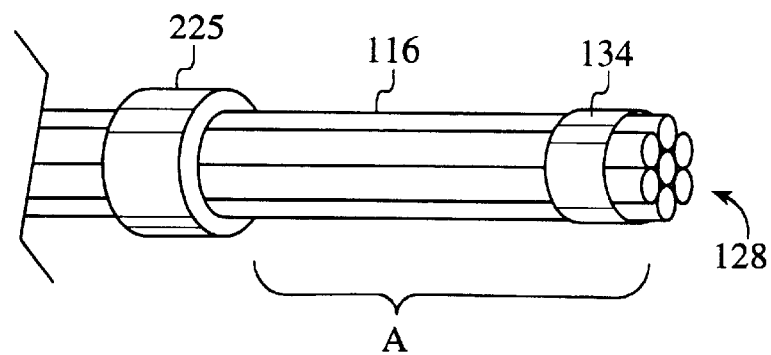
FIG. 2B is a representative isometric view of the distal end of a preferred embodiment of a laser delivery device of the present invention.
Figure 3:
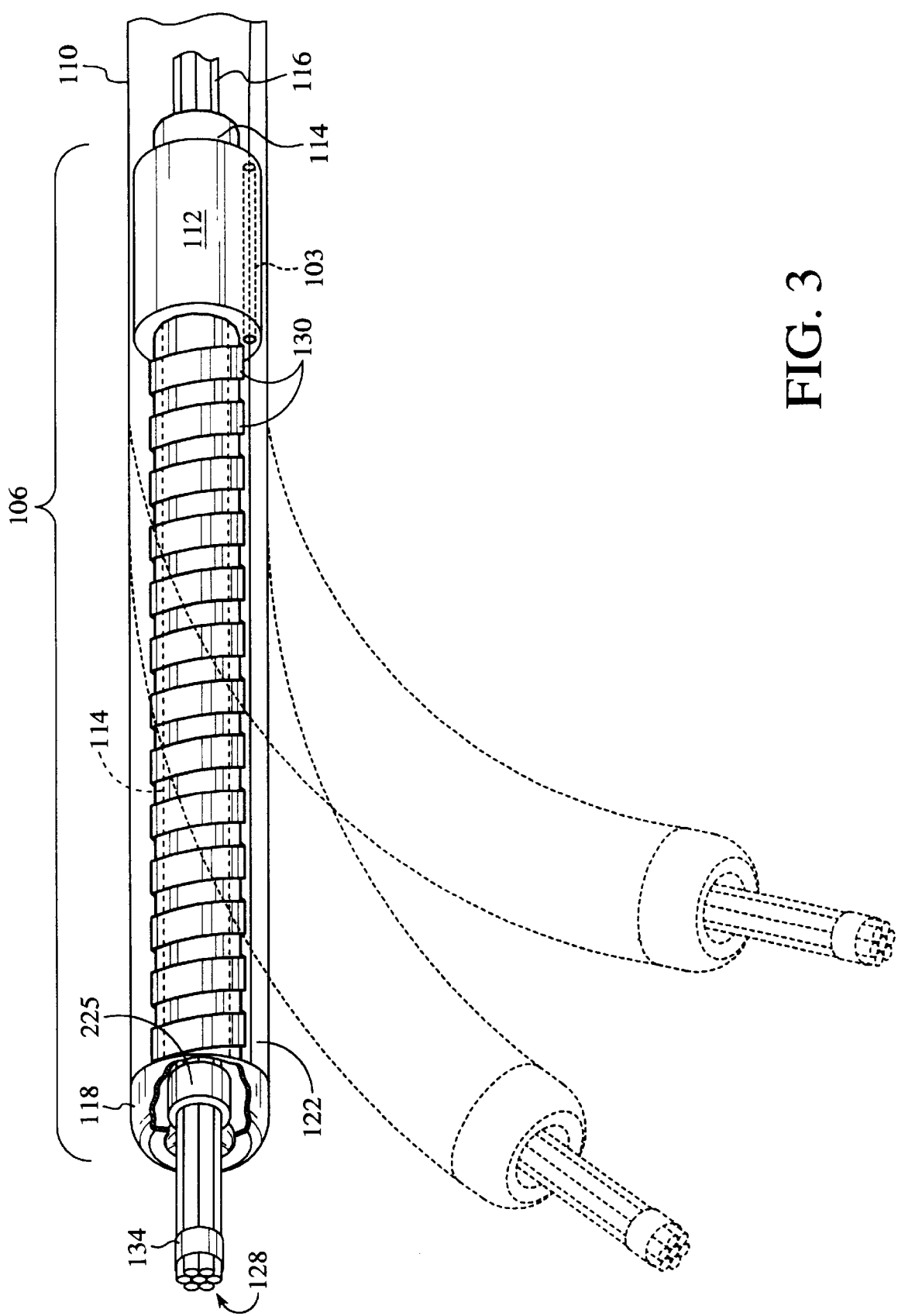
FIG. 3 is a representative partial cutaway view of the deflectable end portion and anchor sleeve of another preferred embodiment of the steerable catheter of the present invention.

FIG. 2B is a representative isometric view of the distal end of a preferred embodiment of a laser delivery device 116 of the present invention. Adjacent the distal end 128 of the optical fiber, fiber bundle or other laser delivery device 116, a ring member 225 which has a greater diameter than fiber 116 is attached so as to engage the catheter tip 118 and perform as an optional fiber displacement stop. Placement of the ring 225 along optical fiber or fiber bundle 116 is selected to control depth, as shown by length A, of created pathways into the myocardium. Radiopaque marker 134 is shown as well. FIG. 3 is a representative partial cutaway view of the deflection end portion 106 and anchor sleeve 112 of another preferred embodiment of the steerable catheter 100 of the present invention. Pull cable 122 is attached at a location near the tip 118 and extends through pull cable guide 103. The deflectable end portion 106 is made out of a softer material than the proximal shaft catheter jacket I 10. As the pull cable 122 is pulled, a force is applied to the catheter tip 118 resulting in tip deflection as shown in the phantom views. This design relies upon the flexibility of the spring 130 to provide the necessary return force instead of a shim as in the design shown in FIG. 2A. The spring 130 in any of these figures may be made of various materials known to those of skill in the art including, but not limited to, stainless steel, tungsten, or even partially or completely constructed of one or more superelastic and/or shape memory materials. Cross section of wire of the spring may be for example, oval, round, rectangular or flat ribbon.

Figure 4:
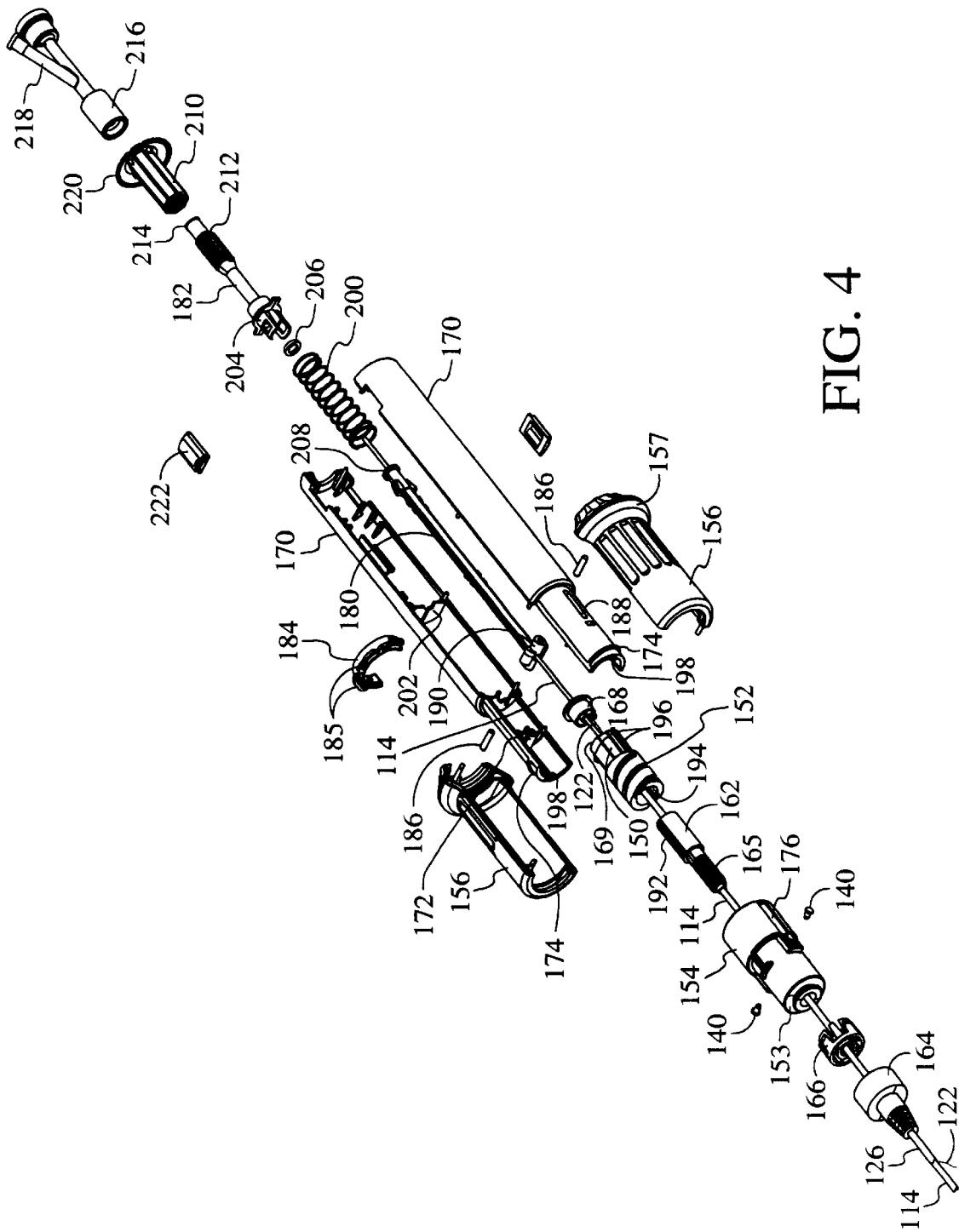
FIG. 4 is a representative exploded view of the internal assembly of a preferred embodiment of the handle of the steerable catheter of the present invention using a rotatable differential screw mechanism with an integrated functional device advance mechanism for achieving auto-alignment of the distal tip of the catheter and functional device.

As seen in FIGS. 4 and 5, outer catheter jacket 110 terminates at its proximal end 126 and is coupled to catheter base 162. Proximal hub 166 is contained within the catheter boot 164 and threads over inside stepped and threaded portion 165 of catheter base 162. The proximal hub 166 is coupled to a distal flange portion 153 of inner deflection knob 154. Deflection actuator 150 slides over catheter base 162 and has an external helical grooved portion 152 located distally on the deflection actuator 150. Two pins 140 attached to inner deflection knob 154 engage helical groove 152, thus rotation of inner deflection knob 154 about deflection actuator 150 translates into linear motion between inner deflection knob 154 and defection actuator 150. An actuator 156 (shown in two sections in FIG. 4) couples radially around the inner deflection knob 154 and translates linearly with respect to inner deflection knob 154. The actuator 156 engages inner deflection knob 154 at flange 158.

The inner tube 114 is attached to handle 170 at coupling point 172. A distal external, helical rib or thread 174 on the handle 170 fits into and acts in cooperation with an operatively pitched and contoured internal helical slot or groove 176 located proximally on the inner deflection knob 154. The inner tube 114 continues proximally, sliding through a front tube 180 and terminates within a back tube 182. A bushing 184 is mounted on bushing pins 186 which extend through longitudinal slots 188 located distally within handle 170 and extend into pin seats 190 located distally on front tube 180. Thus, as the front tube 180 is moved linearly with respect to the handle 170, the bushing pins 186 move linearly within slots 188.

Relative motion between the front tube 180 and the handle 170 is limited to linear motion; there is no rotational motion between the front tube 180 and the handle 170 as such is prevented by the bushing pins 186 which only slide linearly in slots 188. Similarly, axially and longitudinally extending ribs or keys 192 located proximally and externally on catheter base 162 slide linearly within correspondingly shaped linear grooves 194 located internally and distally on deflection actuator 150 opposite the external helical groove 152, thus preventing rotational motion as between the catheter base 162 and the deflection actuator 150. Finally, axially and longitudinally extending ribs or keys 196 located proximally and externally on deflection actuator 150 slide linearly within correspondingly shaped linear grooves 198 located internally and distally on handle 170 at a point distal to slots 188, thus preventing rotational motion as between the deflection actuator 150 and the handle 170.

Pull cable 122, such as shown in FIGS. 2A and 3, extends proximally from the catheter tip 118 through the catheter base 162 and through the deflection actuator 150, and terminates at pull cable stop 168. Pull cable 122 biases pull cable stop 168 against the proximal end 169 of deflection actuator 150.

The actuator 156 rotates around the bushing 184 and the entire assembly including the actuator 156, the bushing 184, bushing pins 186 seated in the front tube 180 along with the front tube 180, back tube 182 and proximal assembly all translate linearly. Additionally, as the actuator 156 is rotated about a central axis, the inner deflection knob 154 is co-operatively and simultaneously similarly rotated thus effectuating linear translation of deflection actuator 150 and thereby increasing tension in pull cable 122. To prevent the contractive forces on the pull cable 122 which deflect the catheter 100 and translate into counter-rotational forces on the actuator 156 from actually causing the assembly to essentially unwind", therefore, bushing 184 is constructed with several detents 185 which compress between actuator 156 and handle 170 distally. In a preferred embodiment of the bushing 184, therefore, the resilient detents 185 are distributed around the bushing 184 so as to engage one or more correspondingly shaped grooves, indentations within the proximal flange 157 on actuator 156.

Therefore, as the actuator 156 is rotated in a first direction so as to cause deflection of the deflectable portion 106 of the catheter 100, engagement of the detents 185 of the bushing 184 within the proximal flange 157 of the actuator 156 provides an indexed mechanism, which allows a tactile response by the physician so as to control or at least be aware of the degree of deflection caused by said rotation of the actuator 156. Furthermore, engagement of the detents 185 of the bushing 184 within the proximal flange 157 of the actuator 156 prevents uncontrolled counter-rotation caused by the above described contractive forces developed in the pull cable 122 of the deflected catheter 100. Upon intentional counter-rotation by the physician, resilient detents 185 deform and allow rotation of the actuator 156 as desired. Thus, bushing 184 is designed with resilient detents 185 which provide directionality, i.e., they provide a certain degree of resistant to rotational forces on the actuator 156 intended to deflect the catheter 100 but provide an increased resistance to counter-rotational forces, thereby providing an indexed mechanism with tactile response upon rotation in either direction.

The handle 170 retains a portion of the back tube 182, the back tube 182 slidable through the handle 170 and biased proximally by spring member 200; the spring member 200 is retained between standing rib member 202 extending internally from handle 170 and distal flange 204 on back tube 182. A sealing member 206 is placed between a proximal flange 208 on the front tube 180 and the distal flange 204 on the back tube 182. A depth stop 210 is threaded onto external helical threads 212 of back tube 182 extending proximally from handle 170. A Luer fitting 214 or other suitable coupling and sealing device is useful for coupling a Touhy-Borst type fitting 216 to the back tube 182. An optical fiber, fiber bundle, or other laser energy delivery device or other functional device may be coupled securely to the Touhy-Borst type fitting 216 and be advanced through the back tube 182 and into the inner tube 114. A saline flush, drug solution, visualization or other therapeutic agent containing fluid can be provided to the steerable catheter via one branched arm 218 of fitting 216. In a preferred embodiment, it will be understood that any back-flow preventer, check valve, blood seal, etc. with the necessary operative function and suitability can be employed elsewhere on the steerable catheter 100 and will be included within the scope of the present invention.

During a PTMR procedure using a steerable catheter as shown in FIG. 1, maintaining alignment between the fiber tip 128 and catheter tip 118 is preferred for controlling channel depth in a heart wall. The distal tip 128 and catheter tip 118 must manually be realigned during deflection in the steerable catheter 100 as taught in U.S. patent application Ser. No. 08/833,352.

Figure 6A:
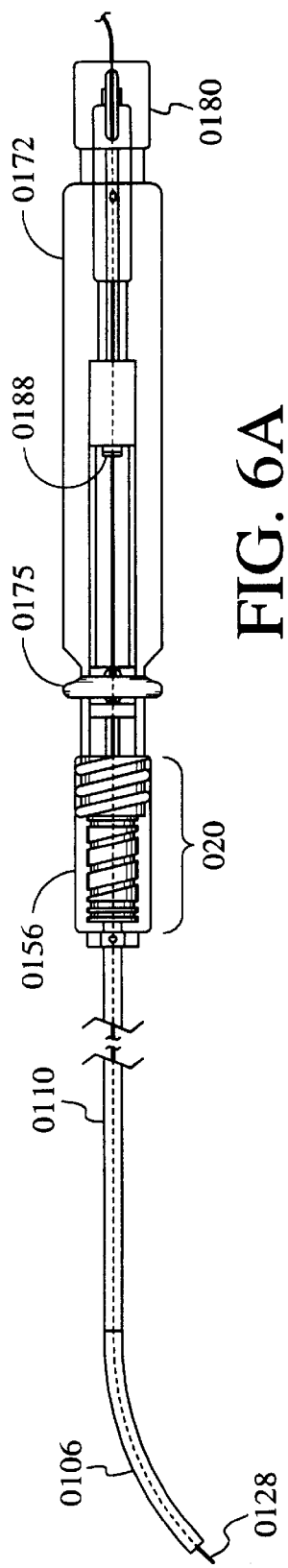
FIGS. 6A–6C are representative isometric cutaway views of the steerable catheter of the present invention illustrating a preferred embodiment of the method of the present invention.
Figure 6B:
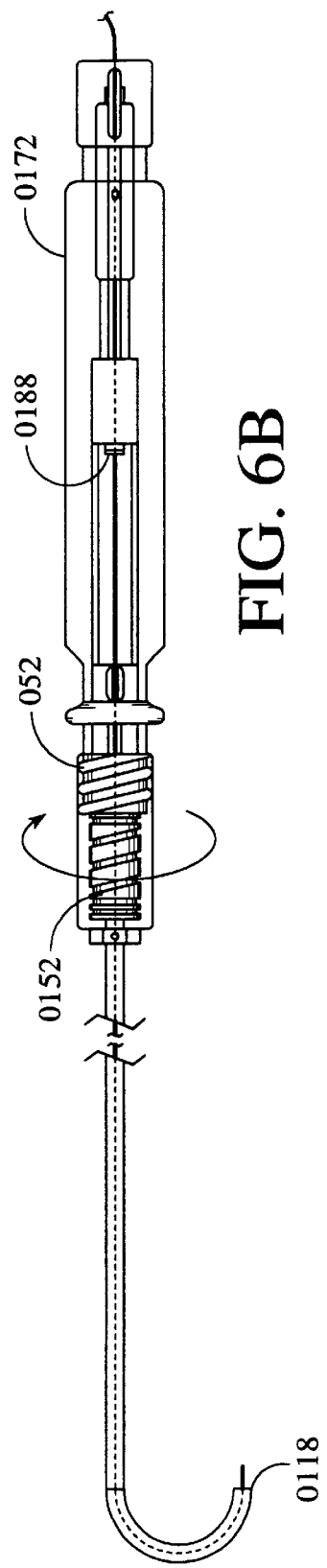
Figure 6C:
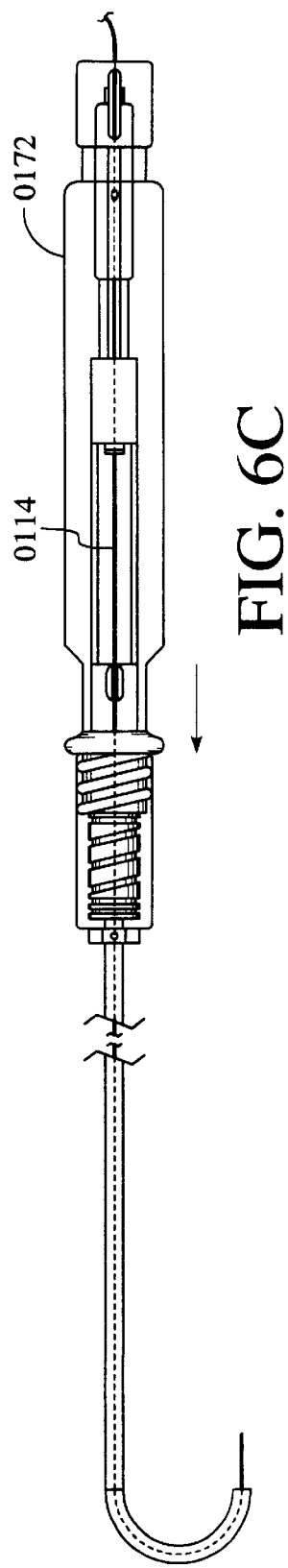

FIGS. 6A, 6B and 6C show an automatic tip alignment mechanism for a steerable catheter system using a differential screw mechanism 020 within deflection knob 0156. The differential screw member within the knob 0156 has two differing thread pitches where threads 0152 effectuate tip deflection and threads 052 effectuate tip alignment compensation. When the deflection knob 0156 is turned, a corresponding advancement or retraction of the catheter's outer jacket occurs causing handle section 0172 to move in relation to the proximal region of center or inner tube 01 14 and the optical fiber thereby maintaining optical fiber alignment. FIGS. 6A and 6B show the sequential deflection of the distal tip section as the deflection knob 0156 is turned. FIG. 6A shows the catheter distal section 0106 without fiber advance, FIG. 6B shows the distal section 0106 deflected and FIG. 6C shows the distal section 0106 deflected with advancement of optical fiber tip 0128. The diaphragm valve 0188 acts as a seal component to prevent saline solution, if used, from being emitted from the handle while still allowing translation of the optical fiber. An optical fiber is inserted into the inner tube 0114 and the fiber distal tip 0128 and catheter tip 0118 (as shown in FIG. 1) are adjusted and aligned manually prior to use. As the deflectable tip section 0106 is deflected as shown in FIG. 6B, the differential screw in deflection knob 0156 causes relative motion of the catheter jacket 0110 and handle 0172 that is attached to the optical fiber advance mechanism thereby maintaining the alignment between the fiber distal tip 0128 and catheter tip 0118 with the improved auto-alignment knob incorporated in the handle 0172. FIG. 6C shows distal section deflected with the fiber advanced using a ring-type knob 0175 which surrounds the handle section 0172 and facilitates fiber advancement to a preset depth according to a setting made with depth control knob 0180.

FIG. 6D shows a cross-sectional view of the deflection knob 0156 with the catheter base 0162. The threads 0152 for effectuating deflection of the catheter's distal end 0118 are engaged by a pin 025 attached to the deflection knob 0156. The tip alignment compensation threads 052 inside proximal section of the deflection knob 0156 are engaged by another pin 027 attached to the deflection housing tube 0150. The pull wire 0122 is attached at a stop connected to the deflector housing tube 0150. When the deflector knob 0156 is turned, the deflection housing tube 0150 translates over the catheter base 0162. The threads create linear translation compensation of the optical fiber distal tip 0128 as the catheter tip 0118 is deflected.

FIG. 6E is a cross-sectional view of a variation of the embodiment shown in FIGS. 6A–6D using an integrated rotatable differential screw mechanism in deflection knob 0156 that further includes an integrated fiber advance component thereby allowing a physician to maintain hand placement while adjusting the amount of deflection by knob 0156 or while advancing an optical fiber. The design shown in FIG.6E in cross-section further includes a fiber advance annular knob 0256 that slides over and rotates with the deflection knob 0156. This sliding aspect is achieved by longitudinal slots 0252 in the outer surface of the deflection knob 0156 and corresponding longitudinal slots in the annular knob 0256. The fiber advance annular knob 0256 replaces the fiber advance knob 0175 shown in FIGS. 6A–6C above. Rotation of the optical fiber advance knob 0256 rotates the deflection knob 0156. Linear advancement of the fiber advance knob 0256 alone without rotation of the deflection knob 0156 advances the optical fiber without tip deflection due to the longitudinal slots 0252 in the deflection knob 0156 guiding longitudinal slots in the fiber advance knob 0256. The advancement of the fiber is achieved through a fiber advance collar 0275 that is attached to the advance slider. The fiber advance knob 0256 has a return spring 0276.

Figure 6F:
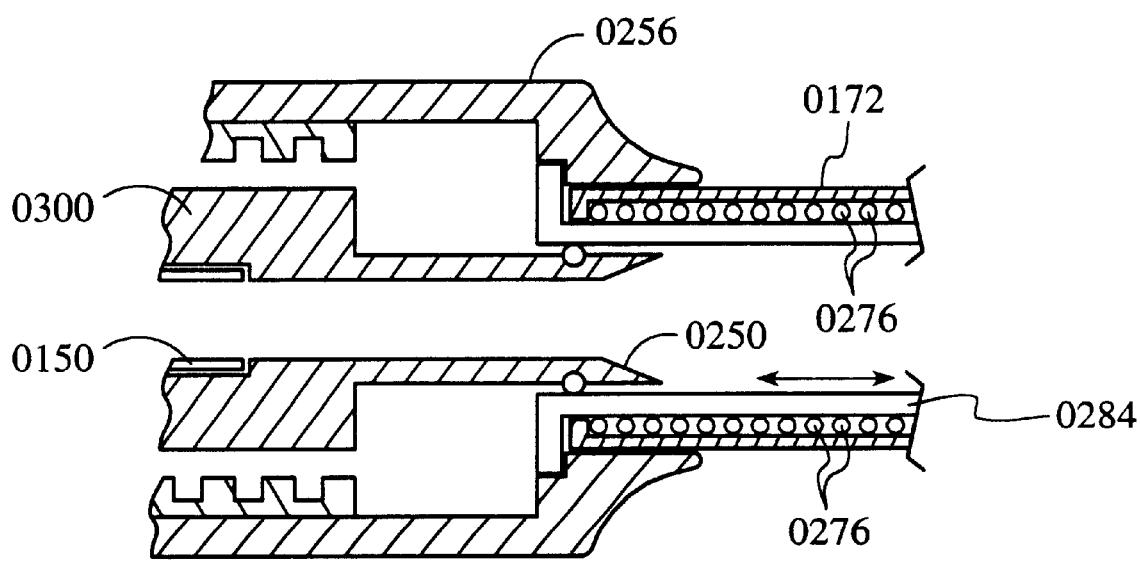
FIG. 6F is a cross-sectional view of a variation of an O-ring sealing member for the optical fiber for the design shown in FIGS. 5C–E and 6A.

FIG. 6F is a cross-sectional view of an alternate design for the functional requirements of the diaphragm valve 0188 sealing device for use with the catheter handle concepts shown in FIGS. 6A–6E. The sealing device is an O-ring 0250 that is disposed about a central member 0300 where the optical fiber translates within the central member 0300. This central member 0300 is attached to the deflection housing tube 0150. An annular extension member 0284 is attached to the fiber knob 0256 shown in FIG. 6B and, slides along on the external side of O-ring 0250 to maintain the fluid seal. An equivalent sealing member of O-ring 0250 is a quad seal. The O-ring seal operates comparable to a "syringe" type device.

The following description of the mechanical operation of the steerable catheter 100 of the present invention is intended for illustrative purposes only, and is not to be construed in any way as limiting the scope of subject matter claimed herein. Reference is made to all of the figures.

As described above, the steerable catheter of the present invention has a tip deflection mechanism as well as a functional device tip alignment mechanism. With regard to FIGS. 4 and 6A–6C, rotation of the actuator 156 in a clockwise direction, i.e., as viewed from a proximal end, will effect corresponding rotation of inner deflection knob 154. Since the actuator 156 and inner deflection knob 154 are rotated relative to the handle 170, and the catheter base 162 is keyed to the deflection actuator 150 by ribs 192 engaging grooves 194 along with the deflection actuator 150 being keyed to the handle 170 by ribs 196 sliding into grooves 198 thereby preventing rotational motion as between the handle 170, the deflection actuator 150 and the catheter base 162, said clockwise rotation will cause proximal translation of deflection actuator 150 by pins 140 riding in helical groove 152, as deflection actuator 150 is moved linearly in a proximal direction, tension in the pull cable 122 acts on the distal tip 118 of the steerable catheter 100 and causes deflection thereof.

Operation of the automatic functional device tip alignment mechanism is based on a screw thread pitch differential. Without the tip alignment feature of the present invention as deflection of the deflectable portion 106 of the steerable catheter 100 occurs the orientation of the distal tip 118 of the catheter 100 and the distal tip 102 of the functional device would be modified such that any pre-existing alignment would be lost. The cause of this loss of alignment between the distal tip 118 of the catheter 100 and the distal tip 102 of the functional device upon deflection of the deflectable portion 106 is caused by retraction of the pull cable 122, causing an apparent change in the length of the elongated catheter jacket 110 and a displacement of any pre-existing alignment between the distal tip 118 of the catheter 100 and the distal tip 102 of the functional device.

Therefore, to compensate for these alignment disrupting forces, screw threads having a differential in pitch size are used. With reference to the drawings, as mentioned above, deflection of the deflectable portion 106 of the catheter 100 is caused by clockwise rotation of the actuator 156 and inner deflection-knob 154. Said clockwise rotational motion of actuator 156 and inner deflection knob 154 causes distal linear translation of inner deflection knob 154, proximal hub 166 and catheter base 162 thereby causing compression of the outer catheter jacket 110 and proximal linear translation of deflection actuator 150 and pull cable stop 168 thereby increasing tension in pull cable 122 and causing deflection of the deflecting portion 106. Simultaneously, as will be apparent by an inspection of the drawings, as inner deflection knob 154 is rotated clockwise by actuator 156, external helical thread 174 on the handle 170 engaged by internal helical groove 176 within inner deflection knob 154 causes simultaneous translation of the handle 170, thus slightly moving the fiber 116 and thereby compensating for the effective change in length of the outer catheter jacket 110 by maintaining alignment between the distal tip 118 of the catheter 100 and the distal tip 128 of the laser energy delivery device 116.

In the case of laser assisted PTMR or other procedures, intervention occurs when an optical fiber, fiber bundle or other laser energy delivery device 1 16 or other functional device is advanced through the inner tube 114 of the steerable catheter and into the patient. Fiber advance is effected in one of two ways—by manually urging in a distal direction either back flange 220 of depth stop 210 or actuator 156. In either case, the fiber, fiber bundle or other laser energy delivery device 116 or other functional device being held firmly in place at the proximal end by Touhy-Borst type fitting 216 advances distally along with the back tube 182 and the front tube 180, both sliding over the inner tube 114, the bushing pins 186 extending from the pin seats 190 in the front tube 180 contained by and riding within the slots 188 located distally on the handle 170, thus placing the spring 200 into increased compression. Retraction of the fiber 116 decreases the compressive forces on the spring 200.

In a preferred embodiment of the steerable catheter of the present invention, access port cover plate 222, as shown in FIGS. 1 and 4 can be removed and any operative device, electrical contacts such as thin coaxial or other electrical traces, leads, conductors, etc. can lead through at least the outer catheter sheath and be utilized at any of various positions on the handle 170, elongated portion 110 or distal tip 118 of the steerable catheter 100 of the present invention. In particular, the distal tip 118 can be provided with a positioning sensor or visualization device, for providing any of various signals from any of various types of sensor or analyzer equipment, such as the ultrasound ranging methods and devices shown and described in U.S. patent application Ser. No. 08/852,977 filed May 7, 1997 entitled ULTRASOUND DEVICE FOR AXIAL RANGING which is hereby incorporated herein by reference in its entirety. In a preferred embodiment, an annular ultrasound transducer is positioned distally on the distal tip 118 to transmit ultrasound signals substantially perpendicular to tissue, the transducer further receiving returning signals from the tissue to be treated.

U.S. application Ser. No. 08/773,872 entitled LASER MEANS ADAPTED FOR DRUG DELIVERY filed Dec. 27, 1996, and hereby incorporated by reference in its entirety, discloses a drug delivery apparatus for dispensing a predetermined amount of one or more drugs in, near or around the creation of one or more laser-created openings or channels, particularly PTMR channels and/or stimulation pockets within myocardium or other stimulation zones to stimulate angiogenesis on or in selected target surfaces in the body. The apparatus includes a laser delivery device such as an optical fiber or fiber bundle having one or more conduits for transmitting drugs included as a part of the delivery device. The conduit may comprise a space along a fiber optic cable between an outer jacket of the cable and the fiber optic, or fiber optic bundle, and an aperture or array of apertures in the end of the cable through which the drug escapes. The aperture or apertures can be replaced with a semi-permeable or permeable membrane, strainer, set of leach holes, etc. Or the conduit may be one or more drug tubes contained in the fiber bundle and the drug exits out of the target end surface of the cable. Or the conduit may be one or more tubes between the fiber optic delivery means and the outer jacket. A piercing device may be mounted on the target end of the laser delivery means, or an optical fiber with a pointed tip which pierces the target area prior to applying the laser beam may be used. After or simultaneously with the creation of a laser TMR channel or other opening the drug or drugs are transmitted through the conduit directly into the TMR channel or other opening. The target surface may be mechanically pierced to provide initial access to the target region of tissue, such as myocardium. The drug is dispensed by manually or automatically activating an electric motor which actuates a piston element.

Figure 7A:
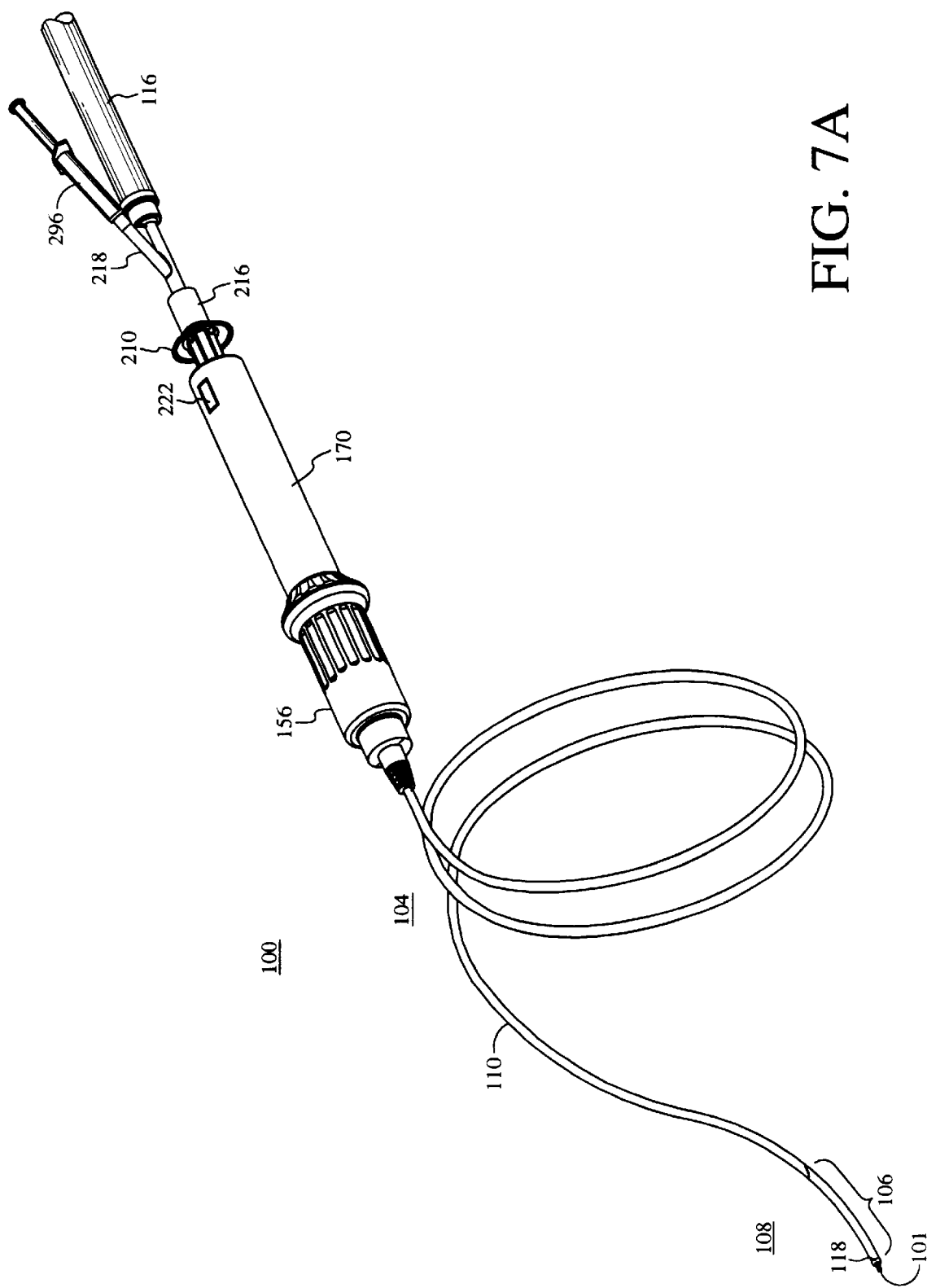
FIG. 7A is a representative isometric view of a drug delivery apparatus coupled to the proximal end of the handle of the steerable catheter of the present invention.

FIG. 7A is a representative isometric view of an alternate embodiment of the present invention with a drug delivery apparatus 296 coupled to the proximal end 104 and a drug delivery needle 101 extending beyond the distal end of the steerable catheter 100 of the present invention. As shown, other tools or functional devices may be attached to the handle 170 of the steerable catheter 100 of the present invention for operation through the inner tube 114 in addition to the drug delivery or dispensing apparatus 296. It will be understood, therefore, that such drug delivery or dispensing apparatus 296 can be manually or automatically activated, can be adjustable or programmable to dispense individual aliquots of a predetermined volume, at a predetermined or specified rate, as desired.

Figure 7B:
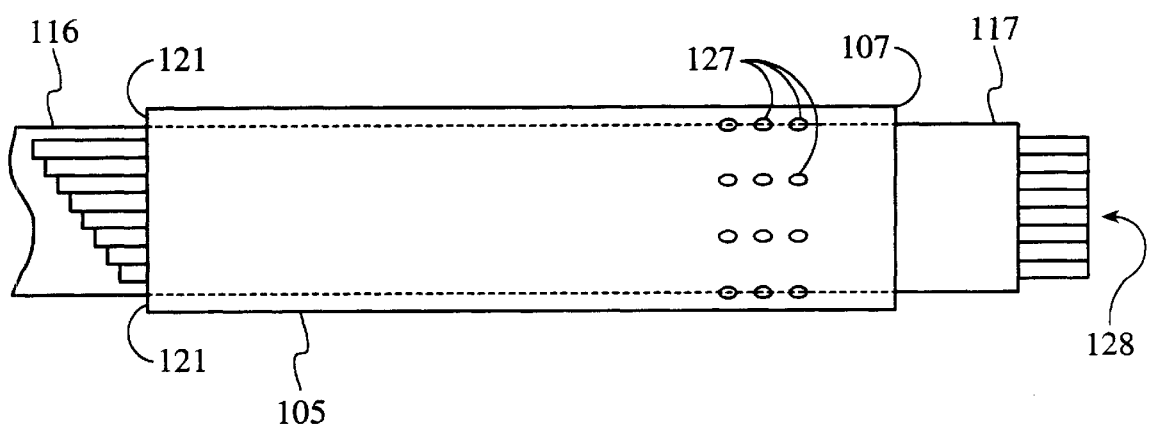
FIG. 7B is a representative side view of an alternate embodiment of a laser delivery device adapted for drug delivery of the steerable catheter of the present invention.

FIG. 7B is a representative side view of an alternate embodiment of a laser delivery device adapted for drug delivery of the steerable catheter of the present invention. The laser delivery device 116 will be disposed within a drug conduit 105. The distal end 107 of the drug conduit 105 has a plurality of (i.e. one or more) perforations 127 formed through the wall of drug conduit 105 allow drugs in space 121 to flow or otherwise be transmitted through drug conduit 105.

The distal end 128 of the laser delivery device 116 preferably extends past the distal end 107 of the drug conduit 105. The laser delivery device 116 may consist of a single or bundle of individual optical fibers.

Outer jacket 117, such as a thin plastic tubing material, surrounds the bundle of individual fibers (as shown in FIG. 7B), and thus, the combination of outer jacket 117 and drug conduit 105 defines an interstitial drug channel 121 through which drugs can be conveyed through conduit 105 and out the plurality of perforations 127. It will be understood that the outer jacket 117 is optional and may be omitted. In such case, utilizing a single fiber mounted within conduit 105 will result in drug delivery from the plurality of perforations 127 in essentially the same manner as described above.. However, in the case of a bundle of fibers without an outer jacket 117, drug solution or other substances will flow around each of the individual fibers of the bundle, thus resulting in percolation of drug out of the drug conduit 105 at either or both the plurality of perforations 127 and the distal end of the fiber bundle.

In the embodiments shown, individual perforations 127 are spaced about outer jacket 117. It will be understood that more or fewer perforations may be used, and perforations located at various axial positions located adjacent the distal end 107 of the drug conduit 105.

U.S. patent application Ser. No. 09/080,175 now U.S. Pat. No. 6,183,444, entitled DRUG DELIVERY MODULE, filed May 16, 1998, and hereby incorporated by reference in its entirety, teaches a drug delivery device with a drug delivery needle for percutaneous catheter based procedures. The elongated portion of the device comprises a single or multi-lumen flexible shaft for containing at least one drug delivery channel in a drug delivery tube. A connector tube extends through a catheter mount and is sealed to a drug conduit. The drug conduit extends through an elongated tubular portion of the catheter to the distal tip of the elongated portion where the drug conduit connects to a piercing needle. The piercing needle end portion has a bevel cut end tip or other operable tip for piercing tissue and delivering drug or other compound there through. The drug delivery conduit with piercing needle is inserted through the working channel of the device to treat the desired number of drug delivery tissue sites. The drug flow is communicated from a reservoir through drug conduit and is dispensed through piercing needle subsequent to advance of piercing needle through the distal tip of device. Drugs can be delivered to tissue via advanceable drug conduits with piercing needle tips which pass through a working channel of the instrument.

Figure 8A:
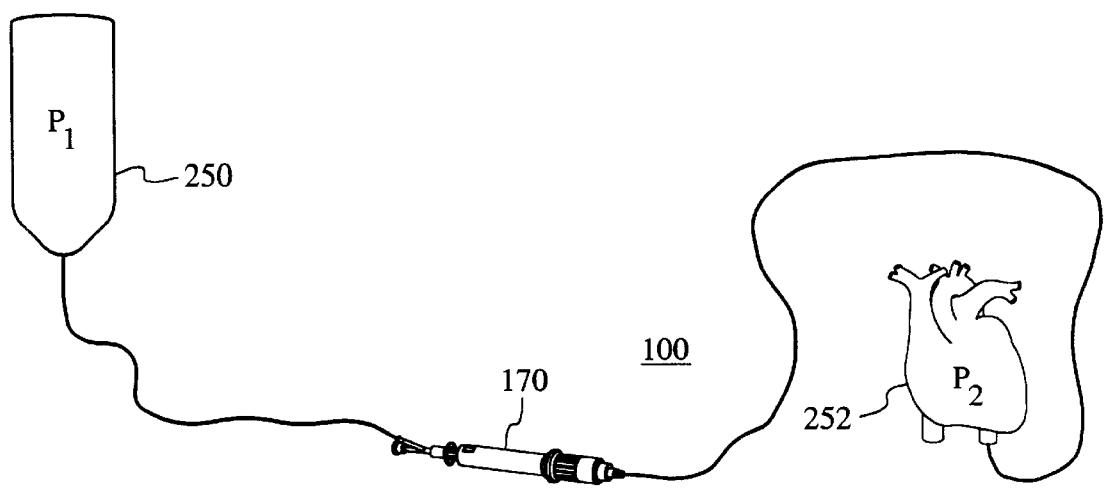
FIG. 8A is a representative schematic view of an alternate embodiment of the steerable catheter of the present invention with a pressurized saline bag.

FIG. 8A is a representative schematic view of an alternate embodiment of the present invention with the steerable catheter and a pressurized saline bag. Reference is made to all the figures. During percutaneous procedures, including PTMR, a saline drip or irrigation system 250 is employed. In the practice of this invention the saline bag can be replaced with any fluid, in any type of reservoir or source. Providing a slightly elevated pressure within the catheter keeps the inner tube 114 of the catheter 100, within which the fiber, bundle or other laser energy delivery device 116 or other functional device 102 advances and retracts, lubricated. Additionally, blood from the ventricle or other portion of the vasculature will not be able to advance past the tip 118 of the catheter 100 and foul or plug the inner tube 114.

During PTMR, saline or other solution flows from a pressurized saline bag 250 through an arm 218 of a Touhy-Borst fitting 216, through the inner tube 114 to the distal tip 118 of the catheter 100 operatively positioned or emplaced within the heart 252. Maintaining a small amount of saline flow through the unrestricted system can readily be achieved. Additionally, a pressurized source may be achieved by elevating the saline bag above operational height, utilizing a small peristaltic or other type of pump to pump the fluid from the saline bag into the vasculature and ventricle, against ventricular pressure, or other type of pump, etc., as may be necessary.

Thus, when the distal tip 118 of the catheter 100 is not in direct contact with an interior body surface, such as the heart wall, a pressure drop would be present:

$$P_1 - P_2 \quad (1)$$

If the distal tip of the catheter is pressed against the heart wall with sufficient pressure to stop the saline or other fluid flow, the pressure throughout the flow path will be at essentially $P_1$, the pressure differential $P_1 - P_2$ will decrease to zero.

Figure 8B:
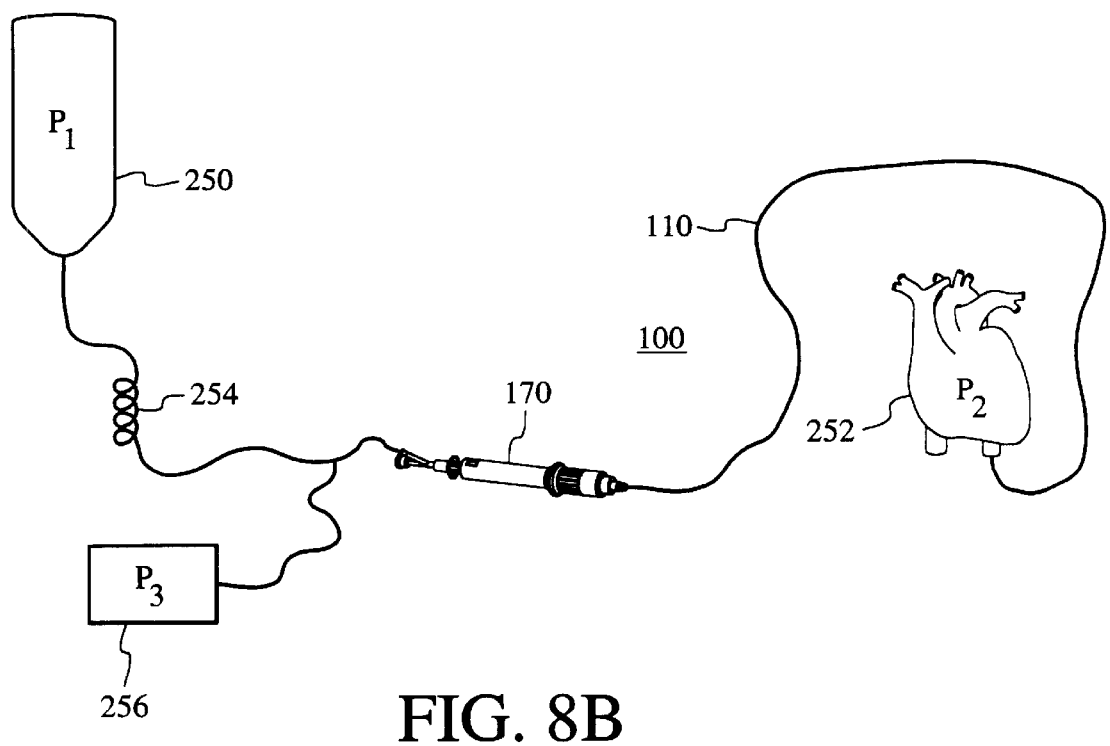
FIG. 8B is a representative schematic view of a preferred embodiment of the steerable catheter with surface contact detection system of the present invention.

FIG. 8B is a representative schematic view of a preferred embodiment of a steerable catheter with heart wall or surface contact detection system of the present invention. By utilizing the system of the present invention to detect saline or other fluid flow through the system, contact with an interior body surface, such as the heart wall, can be determined accurately and dependably. Between the source of pressurized saline solution 250 and the catheter handle 170, a flow restrictor 254 is emplaced. Such flow restrictor 254 may, in preferred embodiments, consist of a restriction valve, a predetermined length of narrow diameter tubing, or a Touhy-Borst etc. Additionally, a pressure sensor 256 is utilized. If the pressure drop across the flow resistor 254 is selected such that it is approximately equivalent to or greater than the pressure drop across the catheter 100, then the pressure $P_3$ at the sensor 256 can be expressed by the following expression:

$$P_3 \approx \frac{(P_1 - P_2)(R_C)}{R_C + R_R} + P_2 \quad (2)$$

where:

$P_3$ = pressure at the sensor 256;
$P_2$ = pressure in the heart;
$P_1$ = pressure in saline bag;
$R_C$ = resistance to flow through the catheter; and
$R_R$ = resistance to flow through the flow restrictor.

When saline solution is flowing in the system, $P_1$ is greater than $P_3$. If the saline flow is decreased due to application of pressure between the distal tip 118 of the catheter 100 and the heart wall, $P_3$ will increase. As the flow stops completely, $P_2$ equals $P_1$ and $P_3$ also equals $P_1$. This system provides the physician with a great deal of additional information. Contact between the distal tip 118 of the catheter 100 and the heart wall can be determined by an increase in $P_3$, as well as the amount of pressure used between the distal tip 118 of the catheter 100 and the heart wall. As more pressure is applied to the heart wall by the distal tip 118 of the catheter 100, $P_3$ will increase until flow of saline through the system stops and $P_3$ becomes equal to $P_1$.

Alternatively, in another preferred embodiment, the laser delivery device 116, or other functional device 102, can incorporate within, or otherwise comprise, an inner lumen 114A (not shown) which is in fluid communication with the pressurized fluid source. Such inner lumen provides a pathway for the pressurized fluid which is less affected by the deflection of the distal tip of the catheter than a device without the inner lumen. Inner lumen 114A is to be interpreted broadly to include any free area or space within the device 116, 102 suitable for fluid transmission in accordance with the present invention. For example, with reference to FIG. 7B, it will be understood that the space between the optical fibers and confined by the outer jacket 117 is considered one form of inner lumen 114A.

While saline can flow between the laser delivery device 1116 or other functional device 102 and the catheter body 110 for lubrication purposes, it is the saline or other fluid which flows within the incorporated inner lumen 114A which is utilized in tissue contact determination as described in greater detail herein. When the catheter is connected to a pressurized fluid source, fluid is allowed to flow through the catheter 100 even though the distal portion of the catheter body 110 and the functional device 102 therein may be deflected. However, when the distal tip of the catheter is in contact or inserted into heart tissue the resistance to flow increases which causes the flow to slow or stop. Such a configuration is advantageous since a separate lumen within the laser delivery device 116 or other functional device 102 will be less affected by pressure changes due to deflection of the distal portion of the catheter 100 resulting in more accurate pressure measurements.

Figure 8C:
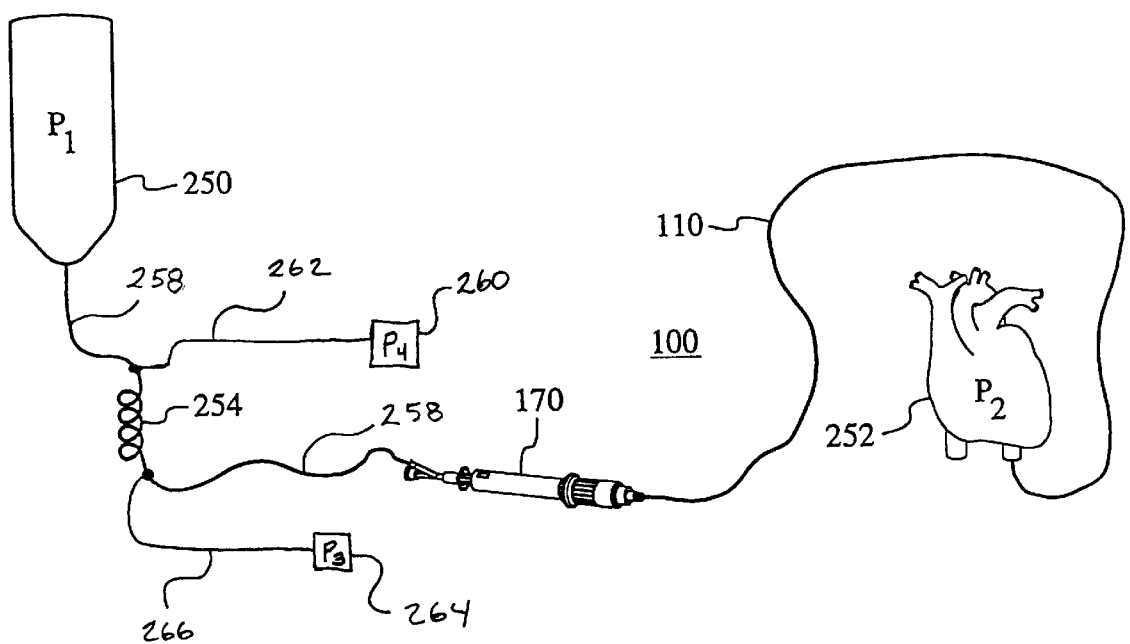
FIG. 8C is a representative schematic view of another preferred embodiment of the steerable catheter with surface contact detection in accordance with the present invention.

With reference to FIG. 8C, an alternative flow estimation apparatus in accordance with the present invention is described. By utilizing two pressure transducers 260, 264, an improved estimation of the flow rate of liquid through the system can be obtained. As with the FIG. 8B embodiment, the pressurized liquid reservoir 250 is connected to and in fluid communication with flow restrictor 254 and steerable catheter 100 through the use of a liquid filled tube 258. The liquid filled tube 258, as part of the catheter 100, can be implemented as inner tube 114, inner tube 114A, any other fluid conduit described herein, or any combination thereof.

The embodiment of FIG. 8C further comprises two air filled tubes 262, 266 which are in fluid communication with the liquid tube 258. The first air filled tube 262 connects to the liquid tube 258 proximal to flow restrictor 254 and the second air filled tube 266 connects to the liquid tube 258 distal to flow restrictor 254. Each of the air filled tubes 262, 266 passes through a liquid detector and microbial or other suitable filter (not shown) prior to engaging a fitting allowing connection to pressure transducers 260 and 264, respectively. The liquid detector may be any suitable device for distinguishing between liquid and air. By example only, such a device may be an ultrasonic transducer.

The microbial or other suitable filter maintains the sterile fluid path of the tubing 258 while allowing the transmission of pressure to its corresponding transducer 260, 264. If an insufficient seal between the liquid tube 258, the air filled tube 262, 266 and the pressure transducer 260, 264 is present, pressurized liquid will be allowed to enter the air filled tube 262, 266 and proceed toward the filter. This is undesirable since microbial filters typically fail to perform when in contact with liquid. Therefore, the liquid detector is appropriately placed between the filter and the tube 258 providing an alert that liquid is present in the air filled tube and providing the operator with an indication to clear the tube and check the connection to the pressure transducer. The alert may also provide for an automatic reduction of pressure using the techniques described below with respect to automated pressure control of the reservoir or using pumps to control the flow.

As stated above, using the two pressure transducers 260, 264 allows an estimation of the flow rate of liquid through the system. The flow is proportional to the difference in pressure across the flow restrictor divided by the resistance to flow through the flow restrictor, which may be constant or may vary as a function of the pressure in the system. This variation in resistance may be compensated by using the average pressure in the restrictor. Additionally, the reading from the pressure transducer proximal to the restrictor may be used to either control the pressure in the liquid reservoir or alert the operator that the pressure is too high or low.

Therefore, during use in an RF based PMR system, for example, when the distal tip of the functional device 102, an electrode in this case, is within the ventricle, the estimated flow rate would be relatively high. When the distal tip of the electrode 102 is in contact with the endocardium the flow rate will be seen to decrease. When the distal tip of the electrode 102 is within myocardium, the flow rate would decrease further or stop altogether. Using the estimated flow rates, a system could provide an indication that the electrode is in myocardial tissue and activation of the electrode would be proper. The system may use the flow rate information to establish an interlock prohibiting activation of the electrode unless the electrode is properly placed within the myocardium or other tissue.

Additionally, after application of the RF energy, the desiccation or ablation of the tissue surrounding the electrode may result in an increase in fluid flow providing an indication that the RF treatment was properly applied. This indication may further act to once again prohibit activation of the electrode after the desired level of treatment has been provided.

In order to reduce or eliminate the injection of liquid from the liquid reservoir 250 into the tissue during treatment, a control loop could be implemented. When the estimated flow indicates that the electrode is in the myocardium the pressure of the liquid reservoir is reduced to a level which prevents injection into the tissue but remains high enough so that when the electrode is removed from the tissue positive flow is re-established. These values may be set to one value for all procedures or may be established specifically for the current procedure during a calibration step.

The calibration step would be performed while the electrode is within the ventricle space and not in tissue contact. Calibration is initiated by setting the liquid reservoir fluid pressure to an initial positive value and measuring the fluid flow rate at that pressure. The pressure of the liquid reservoir is then decreased and additional flow rate data points corresponding to current reservoir pressures are acquired. The data points obtained define a 'curve' of flow vs. reservoir pressure. Calibration data would continue to be acquired until the flow stops, or until it slows sufficiently to extrapolate the zero flow reservoir pressure. A 'normal' operating pressure would then be defined as a fixed value above this zero flow pressure. Therefore, when the electrode is detected to be within the tissue the reservoir pressure would be reduced to a value below the 'normal' operating pressure, but higher than the zero flow pressure.

Alternatively, the reservoir pressure could be set at a constant value throughout the procedure which is higher than the zero flow pressure, but lower than the pressure which would lead to injection of liquid into the tissue. The reservoir pressure which leads to injection of liquid into the tissue could be calibrated using a similar technique to the zero flow pressure but performed while the electrode is in the tissue.

While this example has been framed in terms of a functional device transmitting RF energy, the methods described herein are equally applicable to other functional devices, such as additional thermal energy transmitting devices, drug delivery devices, or any other functional device described herein, including devices incorporating the characteristics and functions of one or more such devices. Additional thermal energy transmitting devices include, but are not limited to, laser energy delivery devices, thermally conductive needles, hollow or otherwise, or other devices adaptable to transmit thermal energy.

The pressure in the liquid reservoir could be controllable using a flexible liquid reservoir enclosed within an inflatable diaphragm. The pressure of the diaphragm could be controlled by linear or discrete control of an air pump and release valve connected to the diaphragm, or any other suitable means.

In place of the pressurized liquid reservoir, liquid may be pumped through the center lumen of the catheter using a pump. This pump may be a syringe pump, a peristaltic pump or a diaphragm pump and may be controlled to maintain a desired pressure as described above. If the pump has high accuracy, the pressure sensor on the proximal side of the flow restrictor would not be required since the flow could be derived directly from the pump. Pumps of sufficient accuracy could include a syringe pump or a calibrated peristaltic pump. The peristaltic pump may be calibrated by calculating a conversion factor between number of turns of the pump to the change of weight on a scale which is providing liquid to the pump.

Alternatively, with reference back to FIG. 8A, fluid flow may be measured using an ultrasonic doppler sensor which measures the flow rate of particles in the liquid. Since the liquid in the system will be delivered to the vascular system of the patient, this liquid will likely be saline or other suitable liquid having a low concentration of particulate matter. To allow for ultrasonic measurement, bubbles may be injected into the liquid path by use of an air pump. The air pump would be interfaced with the fluid tube at a point proximal to handle 170. As also utilized above, a microbial filter may be used to maintain the sterility of the system at the interface or air injection point between the air provided by the air pump and the fluid tube.

The fluid with bubbles can then be measured by the ultrasonic sensor. Distal to the ultrasonic sensor, but still proximal to the handle 170, a bubble trap can remove the bubbles preventing the bubbles from entering the catheter 100. An air detector can be placed distal to the bubble trap to detect failure of the trap and provide the operator with an appropriate warning. Alternatively, the air pump may be used to simultaneously remove air from the bubble trap and pump this air to the injection point in a closed loop fashion to prevent the bubble trap from being filled with excessive air.

Other methods for measuring flow in accordance with the present invention include, but are not limited to, variable area flow meters, rotameters or electronic mass flow meters. Additionally, the liquid reservoir may be placed on a weight scale and the observed change in weight divided by time duration can give an estimation of the flow rate. The volume of liquid in the reservoir could be monitored using a level measurement device such as an ultrasonic level detector or a float measurement system, and the flow estimated as the change in volume divided by time.

This system may also be able to be used in a surgical environment. It may be desirable in a surgical application to avoid activation of the energy device, such as an RF electrode, when a portion of that device is in the ventricle. This situation could be detected using the following technique. While the energy device is outside of the body the estimated flow rate would be high. When the device penetrates the tissue the flow rate is significantly reduced or stopped. When the device extends through the tissue and out the other side, the flow rate will then increase. The device can then be retracted either by a fixed distance, or until the flow rate decreases a sufficient amount to ensure that the device is in the tissue prior to activation or further activation of energy. The RF electrode may include a hollow portion defining inner lumen 114a, as discussed in more detail above. Alternatively, the energy device may be designed without an opening at the distal tip, but with openings on the side of the device slightly proximal to the distal tip on the distal portion to increase the flow differential observed when the distal portion of the device is within tissue versus within the ventricular space.

It should be apparent that methods and devices of the present invention as described herein could be controlled by an operator interpreting displayed readings from the various transducers or other indicators describing system behavior or through more complicated means such as the use of a microprocessor or microcontroller processing system. Such a processing system may also be utilized in the control of energy directed through the functional device 102.

Figure 9:
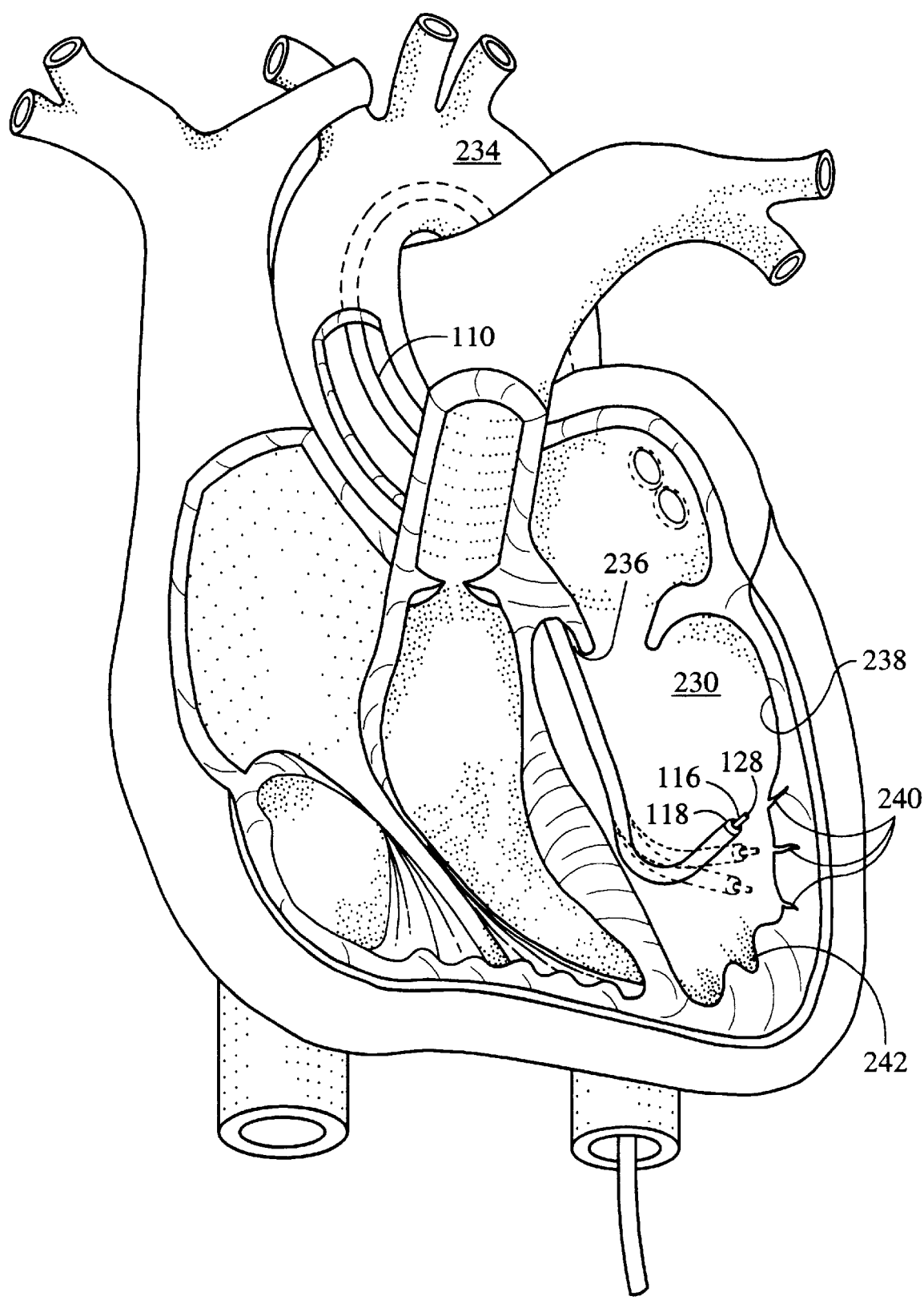
FIG. 9 is a representative perspective view of the steerable catheter of the present invention within the left ventricle.

FIG. 9 is a representative perspective view of the steerable catheter 100 of the present invention within the left ventricle 230. As indicated above and with regard to the figures, the present invention is directed to catheter systems which are steered into and through parts of the body, such as into the left ventricle, with and without the use of a guide catheter or other guide system. Guide catheter and guidance systems are well known and may be used with the present invention, and therefore are included within the scope of this invention. Typically, entry into the vasculature is made through the femoral artery. A guide wire (not shown) is positioned within the left ventricle 230. The steerable catheter 100 is advanced over the guide wire and into the left ventricle 230. The guide wire is retracted out of the steerable catheter and the functional device, such as an optical fiber, is advanced into position with the steerable catheter.

However, a guide wire or guide catheter need not be used. Alternatively, the distal tip 118 and deflectable end portion 106 of the steerable catheter 100 is inserted into the patient, extended over the aortic arch 234 and prolapsed through the aortic valve 236 into the left ventricle 230. The steerable catheter 100 can be guided into a selected position adjacent a selected surface 238, in this case a portion of endocardium. As the actuator 156 is rotated, deflection of the deflectable portion 106 results in slight modification of the dimension of the elongated portion 110 of the catheter 100, the modification compensated for by the differential screw mechanism of the present invention. Furthermore, a wall contact detection system provides wall contact and contact pressure information to the physician.

Thus, by sequential deflection the deflectable end portion 106 of the steerable catheter 100 and/or by rotation of the steerable catheter 100, extending the distal end 128 of a laser delivery device 116 or other functional device therethrough, delivering laser energy or performing other therapy, visualization or diagnostic, and retracting the distal end 128 of the laser delivery device 116 or other functional device back into the deflectable end portion 106, the steerable catheter 100 can treat a series of individual, selected treatment points 240 of tissue such as endocardium. Such treatment points 240 would typically be TMR channels or stimulation sites.

Alternatively, retro-lasing can be performed. This novel method includes the steps of advancing the distal tip 128 of laser delivery device 116 a selected distance into the myocardium and then delivering laser energy to create a TMR channel or other treatment site while simultaneously retracting the fiber, laser delivery device 116 or other functional device. With this procedure, with regard to TMR especially, inasmuch as laser energy is only delivered during retraction of the fiber, the possibility of advancing the fiber too far and lasing through an epicardial surface is decreased, and the risks of complications arising from such epicardial perforations, including but not limited to cardiac tamponade (a buildup of pressure in the pericardial sac caused by the presence of an excess of fluid such as blood), proliferation of adhesion between the epicardium and the pericardial sac (thereby preventing normal, frictionless enclosure of the heart muscle within the pericardial sac), etc. are minimized.

The functional device or devices of the present invention includes those devices for treatment and diagnosis of affected organs, tissues or interiors or interior surfaces of the body, including devices configurable and extendable through one or more lumens within a steerable catheter, for example, energy delivery devices, such as laser optical fiber elements, with or with out a piercing needle, laser wave guides, radio frequency tissue ablation devices, microwave cutters, ultrasound transmitters, mechanical coring devices, fluid jets, or drug delivery devices, with or without a piercing needle assembly.

Furthermore, adjunct use of ancillary drug delivery apparatus, blood seal device, depth stop apparatus such as clamps, bushings, etc., visualization device, marker device as well as other hardware and methodology will be considered within the scope of the present invention.

The alignment mechanism or tip alignment mechanism or automatic tip alignment mechanism of the steerable catheter can be any relative movement compensation mechanism, including, but not limited to, a screw mechanism, for example, a rotatable differential screw mechanism, gear, camming or threaded mechanism.

The present invention is intended for use with any medical laser. In particular, the Holmium or excimer laser is particularly suited to the present invention. However, any suitable laser source, pulsed or otherwise, could provide laser energy to the laser delivery device of the present invention for performing the method of the present invention. Likewise, the steerable catheter and equipment, including laser delivery device, referred to in the present document as well as that known and used in medicine and other disciplines today and in the future, will be included in the scope of this disclosure. Such laser delivery devices include, but are not limited to, individual optical fibers as well as bundles of fibers with and without piercing tips and with or without firing tips or fiber ends having shaped or contoured end faces for selectively diverging the laser beam or other laser energy diverging device, rods, mirrors configurations and other laser delivery device with and without focusing lens and the like. It will also be understood that the steerable catheter and method of the present invention as described herein including the novel combination or use with of any conventional mechanism or method which are known to those skilled in the art, are included within the scope of this invention.

Furthermore, with regard to non-laser TMR, a cannula or trocar assembly may be extended into the tissue of the left ventricle, with or without use of a mechanical piercing tool.

For the purposes of the present invention and disclosure herein, the term "drug" or "drugs" includes any and all drugs and therapeutic agents for use or useable within or on the body, including, but not limited to the following, gene therapies, angiogenic agents, antibiotics, vaccines, function regulators, anti-arrhythmic drugs, growth factors, anticoagulant antagonists, anticoagulants, anti-fibrinolytics, platelet inhibitors, thrombolytics, antihistamines, anti-inflammatory agents, immuno-suppressives, receptor antagonists, adrenergic blockers, adrenergic stimulants, alpha/beta adrenergic blockers, angiotensin converting enzyme inhibitors, angiotensin It receptor antagonists, anti-arrhythmics Group I, Group II, Group III, Group IV, beta blockers, calcium channel blockers, diuretics, hypertensive emergency agents, angiogenic agents, FGF-I, FGF-2, EGF, Vascular Endothelial Growth Factor (VEGF) (preclinical), inotropic agents, patent ductus arteriosus therapy, Rauwolfia derivatives and combinations, vasodilators, vasopressors, adjuncts, androgen inhibitors, antibiotic derivatives, anti-estrogens, anti-metabolites, cytotoxic agents, enzyme inhibitors, hormones, immuno-modulators, nitrogen mustard derivatives, agents used in photodynamic therapy, such as photo-active or photo-labile compounds, and/or other materials for performing functions including flushing and cooling, stimulating other responses, detection, analysis, monitoring, visualization or control, etc., said solutions comprising waters, saline and the like, solid and semi-solid materials, and in any forms including capsules and granules, implants, etc.

The present invention includes the delivery of liquid, solid or semi-solid, time release formulations, etc. It will be understood that there are additional drugs or therapeutic agents which may become useful, such as agents directed at bone or implanted in semi-permeable sacs, radioisotopes, and future gene therapies which are also included in the scope of this invention.

Active compounds which are given systemically have a normal therapeutic window which can be expressed as mg of drug per kg of body weight. The amount of agent which is therapeutically acceptable when administering a drug locally can be approximated as mg of drug per kg of target treatment area (e.g. organ weight), optimized accordingly with consideration of toxicity and mechanism of drug action. Agents delivered to a specific site can achieve high local concentrations at the delivery point. Optimal drug dose may scale differently when the drug is administered locally rather than systemically. Thus, the amount of a given agent that should be delivered in order to achieve a therapeutic effect must be optimized accordingly with consideration of toxicity levels (both locally and systemically), mechanism of drug action, drug clearance mechanisms, and drug diffusion levels.

It will further be understood that while the present invention has been described for performing TMR on endocardial surfaces in the left ventricle, the apparatus and methods described herein are equally intended for use in any suitable procedure, including but not limited to procedures, where any device need be extended through a guide catheter or the vasculature to an opening or other point within the body for other medical procedures including one or more of the following, laser treatment, drug delivery, visualization, biopsy, etc. "Stimulation", for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956 filed Jun. 13, 1996, herein incorporated by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A method of treatment within a body using a steerable percutaneous catheter, the steps of the method comprising:
    a) providing a steerable percutaneous catheter system comprising a catheter having a lumen, a functional device slidably disposed within the catheter lumen and means to measure fluid flow through the catheter;
    b) positioning a distal portion of the catheter within the body;
    c) detecting contact between a target tissue and a distal portion of the catheter, wherein a decrease in measured fluid flow is indicative of tissue contact; and
    d) effectuating treatment.

2. The method of claim 1 wherein the distal portion of the catheter is positioned within the left ventricle and the treatment is the creation of channels in the myocardium.

3. The method of claim 1 wherein the functional device is a laser delivery device and the step of effectuating treatment comprises the step of applying laser energy.

4. The method of claim 1 wherein the functional device is an RF energy delivery device and the step of effectuating treatment comprises the step of applying RF energy.

5. The method of claim 1 wherein the catheter system further comprises a pressurized fluid source, first and second pressure measurement systems operatively attached to the proximal and distal ends of a flow restrictor, respectively, and the step of detecting contact further comprises the step of measuring the pressure difference across the flow restrictor, whereby the fluid flow is proportional to the measured pressure difference divided by the resistance to fluid flow of the flow restrictor.

6. The method of claim 5 wherein the pressurized fluid source comprises saline and the step of measuring the pressure difference comprises measuring the pressure difference of saline.

7. The method of claim 5 wherein the catheter system further comprises a means for controlling the pressure in the pressurized fluid source and the method further comprises the step of controlling the pressure of the pressurized fluid source.

8. The method of claim 7 wherein the step of controlling the pressure of the pressurized fluid source comprises the step of changing the elevation of the pressurized fluid source with respect to the catheter.

9. A steerable percutaneous catheter system with contact detection, comprising:
   a catheter; and
   a means for measuring a fluid flow through the catheter, said means for measuring a fluid flow further comprising:
      a pressurized fluid source comprising an elevated fluid reservoir;
      a first and a second pressure measuring subsystem;
      a flow restrictor;
      a first fluid tube which is in fluid communication with said pressurized fluid source and a proximal end of said flow restrictor; and
      a second fluid tube which is in fluid communication with a distal end of said flow restrictor and a proximal end of said catheter;
   wherein a decrease in said fluid flow is indicative of tissue contact by a distal portion of said catheter, and further wherein a fluid flow rate is proportional to a pressure difference measured by said first and second pressure measuring subsystems divided by a resistance to said fluid flow of said flow restrictor.

10. The system of claim 9 wherein the means for measuring fluid flow comprises an ultrasonic doppler sensor operatively connected to a fluid path of the catheter and sensitive to the movement of particulate matter within the fluid.

11. The system of claim 10 further comprising an air pump operatively connected to the fluid path at a point proximal to the ultrasonic doppler sensor and a bubble trap operatively connected to the fluid path at a point distal to the ultrasonic doppler sensor,
   whereby the air pump injects the fluid with ultrasonically detectable air bubbles and the bubble trap ensures the air bubbles are removed from the fluid path prior to the catheter.

12. The system of claim 11 further comprising an air detector operatively connected to the fluid path at a point distal to the bubble trap,
   whereby air detected in the fluid path distal to the bubble trap can be detected.

13. The system of claim 11 further comprising a filter operatively disposed between the air pump and the fluid path.

14. The system of claim 13 wherein the filter is a microbial filter.

15. The system of claim 9 wherein the means for measuring fluid flow consists of one or more measuring devices selected from the group consisting of a variable area flow meter, a rotameter, and electronic mass flow meters.

16. The system of claim 9 wherein the catheter comprises:
   a catheter jacket having a proximal end, a distal end, and at least one lumen extending therethrough;
   at least one functional device having a lumen defined therein, a first of the at least one functional device disposed within a first of the at least one lumen of the catheter jacket which is in fluid communication with the pressurized fluid source; and
   a tip alignment device at the proximal end of the catheter operatively attached to the catheter jacket and the at least one functional device,
   wherein the catheter and the at least one functional device remain aligned during deflection of the distal end of the catheter.

17. The system of claim 16 wherein the distal portion of the lumen of the at least one functional device defines at least one opening from which the pressurized fluid can egress.

18. The system of claim 17 wherein the at least one opening defines a geometric surface, a central point of the geometric surface lying essentially upon the longitudinal axis of the distal portion of the lumen of the at least one functional device.

19. The system of claim 17 wherein the at least one opening is defined in the side of the lumen of the at least one functional device slightly proximal to the distal tip.

20. A steerable percutaneous catheter system with contact detection, comprising:
   a catheter; and
   a means for measuring a fluid flow through said catheter, said means for measuring a fluid flow further comprising:
      a first and a second pressure measuring subsystem, wherein said first and second pressure measuring subsystems each comprise a first and a second pressure transducer, respectively, and further wherein said first and second pressure measuring subsystems each further comprise a first and second air tube;
      a flow restrictor;
      a first fluid tube which is in fluid communication with said pressurized fluid source and a proximal end of said flow restrictor; and
      a second fluid tube which is in fluid communication with a distal end of said flow restrictor and a proximal end of said catheter;
   wherein said first and second air tube interfaces said first and second pressure transducer to said first and second liquid tube, respectively, and further wherein a decrease in fluid flow is indicative of tissue contact by a distal portion of the catheter wherein a fluid flow rate is proportional to a pressure difference measured by said first and second pressure measuring subsystems divided by a resistance to said fluid flow of said flow restrictor.

21. The system of claim 20 wherein said first and second pressure measuring subsystems each further comprise a filter located within each of said first and second air tube, said filter being able to maintain a sterility of the fluid system while transmitting pressure to said first and second pressure transducer, respectively.

22. The system of claim 21 wherein the filter is a microbial filter.

23. The system of claim 21 wherein the first and second pressure measuring subsystems each further comprise a liquid detector,
   whereby the liquid detector detects liquid within the tube indicative of a pressure leak in the system.

24. A steerable percutaneous catheter comprising:
   a catheter jacket, having proximal and distal ends, and at least a first lumen;
   at least a first functional device within the first lumen of the catheter jacket, the first functional device having proximal and distal ends;
   a deflection mechanism at the proximal end of the catheter, the deflection mechanism operatively attached to a deflector device at the distal end of the catheter jacket, activation of the deflector device by movement of the deflection mechanism deflects the distal end of the catheter jacket and the functional device therein; and a relative movement compensation mechanism for maintaining alignment between the catheter jacket and the functional device whereby movement of the deflection mechanism causes simultaneous movement of the relative movement compensation mechanism.

25. The catheter of claim 24 wherein the relative movement compensation mechanism comprises a groove portion on a deflection actuator which cooperates with a set of thread pins attached to a rotatable inner deflection knob, said inner deflection knob operatively coupled to the catheter jacket.

26. The catheter of claim 25 wherein the deflection mechanism comprises a thread portion on a handle which cooperates with a groove portion on the inner deflection knob.

27. The catheter of claim 26 further comprises a mechanism for limiting the rotational movement within the catheter including one or more detent members extending outward from a bushing member and engaging an actuator, radially coupled to the inner deflection knob.

28. The catheter of claim 27 wherein the deflection device comprises a pull cable, having proximal and distal ends, the distal end of the pull cable attached to the distal end of the catheter jacket and extended through a pull cable guide within an anchor sleeve, the anchor sleeve coupled to the distal end of the inner tube and attached to the catheter jacket, the pull cable further extended through the catheter base and the deflection actuator and attached proximally to a pull cable stop, at the proximal end of the deflection actuator.

29. The catheter of claim 28 wherein the deflection device further comprises a shim, having proximal and distal ends, the proximal end attached to the anchor sleeve and a spring and the distal end of the shim attached to the distal end of the catheter jacket.

30. The catheter of claim 27 wherein said inner tube further comprises a back tube and a front tube and a sealing member there between.

31. The catheter of claim 27 further comprises a depth stop threaded to external helical threads of a back tube, slidably disposed in the handle.

32. The catheter of claim 27 wherein the clockwise rotation of the actuator effects corresponding rotation of the inner deflection knob and relative rotation of the handle and with the counter clockwise-rotation of the actuator the detent members deform and allow rotation of the actuator.

33. The catheter of claim 32 wherein the first functional device is attached to a coupling device, branched with at least a first and second arm, the first functional device is coupled through the first arm and advanceable in an inner tube, said inner tube attached to the handle.

34. The catheter of claim 33 further comprises a second functional device coupled through the second arm of the coupling device.

35. The catheter of claim 34 wherein the second functional device comprises a fluid delivery apparatus.

36. The catheter of claim 35 wherein the second functional device comprises a drug delivery apparatus, having proximal and distal ends.

37. The catheter of claim 35 wherein the distal end of the drug delivery apparatus comprises a drug delivery needle.

38. The catheter of claim 35 wherein the fluid delivery device is attached to a fluid reservoir.

39. The catheter of claim 38 wherein the fluid reservoir contains saline.

40. The catheter of claim 38 wherein the fluid reservoir contains at least one therapeutic agent.

41. The catheter of claim 40 wherein the therapeutic agent is an angiogenesis agent.

42. The catheter of claim 38 further comprises a surface contact detection mechanism wherein the fluid reservoir is maintained at a height above an operational height and further comprises a pump member, for pumping the fluid from the fluid reservoir through the catheter and out the distal end of the catheter jacket.

43. The catheter of claim 42 wherein the surface contact detection mechanism further comprises a flow restrictor, attached between the branched arm of the fitting device and the fluid reservoir, and a pressure sensor, attached between the flow restrictor and the branched arm of the fitting device.

44. The catheter of claim 24 wherein the first functional device comprises a laser delivery device.

45. The catheter of claim 44 wherein the laser delivery device is an optical fiber bundle.

46. The catheter of claim 44 wherein the laser delivery device is an optical fiber.

47. The catheter of claim 46 further comprises the laser delivery device disposed within a drug conduit, having proximal and distal ends, the distal end of the drug conduit having a plurality of perforations.

48. The catheter of claim 24 further comprises an operative device.

49. The catheter of claim 48 wherein the operative device is an ultrasound ranging device.

50. A method of treatment within a body using a steerable percutaneous catheter, the steps of the method comprising:
   a) providing a steerable percutaneous catheter that includes, a catheter jacket having proximal and distal ends, at least a first functional device disposed within the catheter jacket, the functional device having proximal and distal ends, a deflection mechanism at the proximal end of the catheter jacket causing deflection of the distal end of the catheter jacket and a relative movement compensation mechanism for maintaining alignment between the catheter jacket and the functional device attached to the relative compensation mechanism;
   b) positioning the catheter for performance of at least a first procedure in the body;
   c) deflecting the distal end of the catheter jacket with movement of the deflection mechanism causing simultaneous compensating movement of the relative movement compensation mechanism; and
   d) effectuating treatment.

51. The method of claim 50 wherein the first procedure is PTMR, the first functional device is a laser delivery device, the catheter is positioned within the left ventricle and the treatment is the creation of channels in the myocardium.

52. The method of claim 51 further including a second procedure, a drug delivery procedure, a second functional device, a drug delivery device, and the treatment further includes delivery of one or more therapeutic agents to the treatment site in the myocardium.

53. The method of claim 52 further including a third procedure, a stimulation procedure, with treatment further including creation of stimulation zones within the myocardium.

54. The method of claim 51 further including a second procedure, a stimulation procedure, and the treatment further includes creation of stimulation zones within the myocardium.

55. The method of claim 50 wherein the procedure is stimulation, the first functional device is a laser delivery device, the catheter is positioned within the left ventricle and the treatment is the creation of stimulation zones in the myocardium.

56. The method of claim 55 further including a second procedure, a drug delivery procedure, and a second functional device, a drug delivery device, and the treatment further includes delivery of one or more therapeutic agents to the treatment site in the myocardium.

57. The method of claim 50 further including in step a) a fluid reservoir attached to the catheter and said fluid reservoir maintained at a height above an operational height, and a pump member, for pumping the fluid from the fluid reservoir through the catheter and out the distal end of the catheter jacket, and prior to step d) the steps of setting a flow rate for pumping fluid, and monitoring the flow rate to determine contact with a body surface, when the distal end of the catheter is in direct contact with a body surface the flow rate decreased.

58. The method of claim 57 further comprising in step a) a flow restrictor, attached between the catheter and the fluid reservoir, and a pressure sensor, attached between the flow restrictor and the catheter, wherein when fluid is flowing the pressure in the fluid reservoir is greater than pressure at the pressure sensor, and when the distal end of the catheter is in contact with a body surface the pressure will increase.

59. The method of claim 50 step b) further including a guide wire for advancing the device through the vasculature and into position within the body.

60. A steerable percutaneous catheter for treating internal body surfaces the apparatus comprising:

- a catheter jacket having proximal and distal ends, and at least a first lumen;
- at least a first functional device within the first lumen of the catheter jacket, the functional device having proximal and distal ends;
- a relative movement compensation mechanism, for maintaining alignment between the catheter jacket and the functional device therein, comprising a groove portion on a deflection actuator which cooperates with a set of thread pins attached to a rotatable inner deflection knob, said inner deflection knob operatively coupled to the catheter jacket;
- a deflection mechanism, to deflect the distal end of the catheter jacket and the functional device therein, comprising a thread portion on a handle which cooperates with a groove portion on the inner deflection knob;
- a surface contact detection mechanism comprising a fluid reservoir operatively attached to the proximal end of the catheter, maintained at a height above an operational height and a pump member, for pumping the fluid from the fluid reservoir through the catheter and out the distal end of the catheter jacket; and
- whereby movement of the deflecting mechanism causes simultaneous compensating movement of the relative movement compensation mechanism.

* * * * *